US012337006B1

(12) United States Patent
Jacobson et al.

(10) Patent No.: US 12,337,006 B1
(45) Date of Patent: *Jun. 24, 2025

(54) METHODS OF TREATING ISCHEMIC STROKE AT RISK FOR CEREBRAL OR CEREBELLAR EDEMA

(71) Applicant: REMEDY PHARMACEUTICALS, INC., New York, NY (US)

(72) Inventors: Sven Martin Jacobson, New York, NY (US); Thomas W. MacAllister, Montross, VA (US)

(73) Assignee: REMEDY PHARMACEUTICALS, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/039,220

(22) Filed: Jan. 28, 2025

Related U.S. Application Data

(63) Continuation of application No. 18/734,541, filed on Jun. 5, 2024, now Pat. No. 12,251,389.

(60) Provisional application No. 63/644,658, filed on May 9, 2024, provisional application No. 63/642,492, filed on May 3, 2024, provisional application No. 63/637,163, filed on Apr. 22, 2024.

(51) Int. Cl.
*A61K 31/64* (2006.01)
*A61B 17/22* (2006.01)
*A61P 9/10* (2006.01)

(52) U.S. Cl.
CPC .............. *A61K 31/64* (2013.01); *A61B 17/22* (2013.01); *A61P 9/10* (2018.01); *A61B 2017/22082* (2013.01)

(58) Field of Classification Search
CPC ...................................................... A61K 31/64
USPC ........................................................ 514/593
See application file for complete search history.

(56) References Cited

U.S. PATENT DOCUMENTS

| | | | |
|---|---|---|---|
| 5,856,360 A | 1/1999 | Salzman et al. | |
| 8,277,845 B2 | 10/2012 | Jacobson | |
| 8,557,867 B2 | 10/2013 | Simard | |
| 8,946,293 B2 | 2/2015 | Jacobson | |
| 12,251,389 B1 * | 3/2025 | Jacobson | A61K 31/64 |
| 2001/0009907 A1 | 7/2001 | Martin et al. | |
| 2005/0246000 A1 | 11/2005 | Larnard | |
| 2006/0276411 A1 | 12/2006 | Simard et al. | |
| 2010/0092469 A1 | 4/2010 | Simard et al. | |
| 2010/0311639 A1 | 12/2010 | Simard | |
| 2011/0034560 A1 | 2/2011 | Jacobson et al. | |
| 2013/0203853 A1 | 8/2013 | Jacobson | |
| 2014/0171467 A1 | 6/2014 | Simard | |
| 2018/0280325 A1 | 10/2018 | Jacobson | |

FOREIGN PATENT DOCUMENTS

| | | |
|---|---|---|
| JP | 2005-534285 A | 11/2005 |
| JP | 2013-532658 A | 8/2013 |
| WO | 2003079987 A2 | 10/2003 |
| WO | 2012012347 A2 | 1/2012 |
| WO | 2016196113 A1 | 12/2016 |
| WO | 2017062765 A1 | 4/2017 |

OTHER PUBLICATIONS

Pergakis et al., "BIIB093 (IV glibenclamide): an investigational compound for the prevention and treatment of severe cerebral edema", Expert Opin Investig Drug, Dec. 5, 2019; vol. 28, No. 12; pp. 1-22.

Unknown, "Phase 3 Study to Evaluate the Efficacy and Safety of Intravenous BIIB093 (Glibenclamide) for Severe Cerebral Edema Following Large Hemispheric Infarction (CHARM)" Clinical Trials# NCT02864953, Version that was publicly available Apr. 18, 2022; 51 pages.

Final Office Action for co-pending U.S. Appl. No. 18/734,522 dated Jan. 17, 2025 (16 pages).

Cannarsa et al., "Decompressive Craniectomy for Stroke: Who, When, and How", Neurologic Clinic, vol. 40, Issue 2, May 2022; pp. 321-336. (1 page).

Wardlaw et al., "Recombinant tissue plasminogen activator for acute ischemic stroke: an updated systematic review and meta-analysis", The Lancet, vol. 379, Issue 9834, Jun. 23, 2012; pp. 2364-2372.

Simard et al., "Glibenclamide in Cerebral Ischemia and Stroke", Neurocrit Care, Apr. 2014 (Year: 2014); vol. 20, No. 2; pp. 319-333.; 24 pages.

"Clinical Commissioning Policy: Mechanical Thrombectomy for Acute Ischemic Stroke (all ages)", NHS England Reference: 170033P, NHS England (Year: 2019); 20 pages.

Non-Final Office Action in corresponding U.S. Appl. No. 18/734,522 dated Oct. 31, 2024. (13 pages).

BSAT et al. "Acute ischemic stroke biomarkers: a new era with diagnostic promise?" Acute Medicine & Surgery (Year: 2021); 8:e696; 18 pages.

Non-Final Office Action in corresponding U.S. Appl. No. 18/734,388 dated Sep. 19, 2024. (38 pages).

Notice of Preliminary Rejection for Korean Application No. 10-2018-7012950 dated Oct. 1, 2023 (5 pp).

(Continued)

*Primary Examiner* — Raymond J Henley, III
(74) *Attorney, Agent, or Firm* — ROTHWELL, FIGG, ERNST & MANBECK, P.C.

(57) ABSTRACT

The invention relates to the treatment of ischemic stroke at risk of brain swelling using SUR1-TRPM4 channel inhibitors in combination with mechanical thrombectomy. In some embodiments, the methods include treating patients suffering from a large hemispheric infarction. In certain embodiments, patients have a lesion volume of less than 140 cm$^3$ or less than 125 cm$^3$ as measured by MRI DWI or CTP. The patient may have suffered a wake-up stroke. Some embodiments involve treating patients who also undergo decompressive therapy.

30 Claims, 1 Drawing Sheet

(56) References Cited

OTHER PUBLICATIONS

Office Action cited Japanese Patent Application No. 2018-517841, mailed Dec. 19, 2022, 20 pages.
Simard et al., "Glibenclamide-10-h Treatment Window in a Clinically Relevant Model of Stroke", Trans. Stroke. Res., 2012, vol. 3, p. 286-295.
Eurasian Office Action issued in Application No. 201890893 dated Jul. 6, 2022 , 7 pages.
Wikipedia, Bolus, 2022, 2 pages. https://en.wikipedia.org/wiki/Bolus.
Wikipedia, Glibenclamide, 2022, 5 pages. https:1/en.wikipedia.org/wiki/Glibenclamide.
Wikipedia, Central nervous system, 2022, 11 pages. https:1/en.wikipedia.org/w/index.php?title=Central_nervous_system&oldid=6239202 57.
O.V. Vasilevskaya, Combined stroke, Practical Medicine, 2007, Jun. 3, 2022, p. 5-7.
Korshunov Nikolai Borisovich and Garmashov Yuriy Anatolievich, "Decompressive craniotomy in severe brain injury in children" Modern medicine: topical issues, 2014, 7 pages.
Kruglov, "Displacement of median structures | Lateral dislocation", accessed 2022, 3 pages (https://radiographia.info/article/smeshchenie-sredinnykh-struktur-lateralnaya-dislokatsiya).
"Ischemic Stroke," https://www.krasotaimedicina.ru/diseases/zabolevanija_neurology/ischemic-stroke, 2022.
Walberer et al., "Midline-shift Corresponds to the Amount of Brain Edema Early After Hemispheric Stroke—An MR Study in Rats", J. Neurosurg Anesthesiol, 2007, vol. 19, No. 2, pp. 105-110.
Brain Nursing, 2013, vol. 29, No. 1, pp. 29-31.
Japanese Notice of Reasons for Rejection issued in 2021-022562 dated Jan. 18, 2022, 10 pages.
Pallan T.V. et al. "Glyburide in Treating Malignant Cerebral Edema. Blocking Sulfonyl Urea One (SUR1) Receptors", Journal of Vascular and Interventional Neurology, 2014, vol. 7, issue 4, pp. 22-24.
Kimberly W.T. et al. "Glyburide is Associated with Attenuated Vasogenic Edema in Stroke Patients", Neurocrit Care, 2013, vol. 20, issue 2, pp. 193-201.
International Search Report cited in PCT/US2016/055988, dated Mar. 2, 2017, 5 pages.
English translation of Chinese First Office Action cited in application No. 201680066630.6 dated Jan. 6, 2020, 6 pages.
Sheth et al: "Exploratory analysis of glyburide as a novel therapy for preventing brain swelling.", Neurocrit Care, (2014), vol. 21, pp. 43-51.
Kurland et al: "Glibenclamide for the treatment of acute CNS injury.", Pharmaceuticals, vol. 6, (2013), pp. 1287-1303.
Partial European Search Report cited in 16854422.9 dated Apr. 24, 2019, 9 pages.
Official Action cited in EA application 201890893 dated Jul. 5, 2019, 3 pages, translation only.
Simard et al., "Newly expressed SUR1-regulated NCca-ATP channel mediates cerebral edema after ischemic stroke", Nat. Med. Apr. 2006; 12 (4); 433-440.
Notice of Reasons for Rejection issued in Japanese Application No. 2018-517841 mailed Oct. 5, 2020, 5 pages.
The Iowa Clinic, "Traumatic Brain Injury (TBI)." https://www.iowaclinic.com/webres/File/traumatic-brain-injury.pdf, 2013.
Wintermark, et al.; "Imaging Evidence and Recommendations for Traumatic Brain Injury: Conventional Neuroimaging Techniques"; J Am Coll Radiol, Feb. 2015; vol. 12, No. 2, pp. e1-e14.
Ospel et al. "Strength of Association between Infarct Volume and Clinical Outcome Depends on the Magnitude of Infarct Size: Results from the ESCAPE-NA1 Trial." AJNR Am J Neuroradiol. Aug. 2021;42(8): 1375-1379. doi: 10.3174/ajnr.A7183. Epub Jun. 24, 2021. PMID: 34167959; PMCID: PMC8367613. (Year: 2021).
Nehring SM, Tadi P, Tenny S. Cerebral Edema. [Updated Jul. 31, 2022]. In: StatPearls [Internet]. Treasure Island (FL): StatPearls Publishing; Jan. 2023. Available from: https://www.ncbi.nlm.nih.gov/books/NBK537272/. (Year: 2022).
Zazulia et al. ("Progression of Mass Effect After Intracerebral Hemorrhage." Stroke, (1999);30:1167-1173. https://doi .org/10.1161/ 01.STR.30.6.1167.) (Year: 1999).
Non-Final Office Action in corresponding U.S. Appl. No. 18/734,541 dated Oct. 16, 2024 (26 pages).
Notice of Allowance in corresponding U.S. Appl. No. 18/734,541 dated dated Jan. 22, 2025 (12 pages).

* cited by examiner

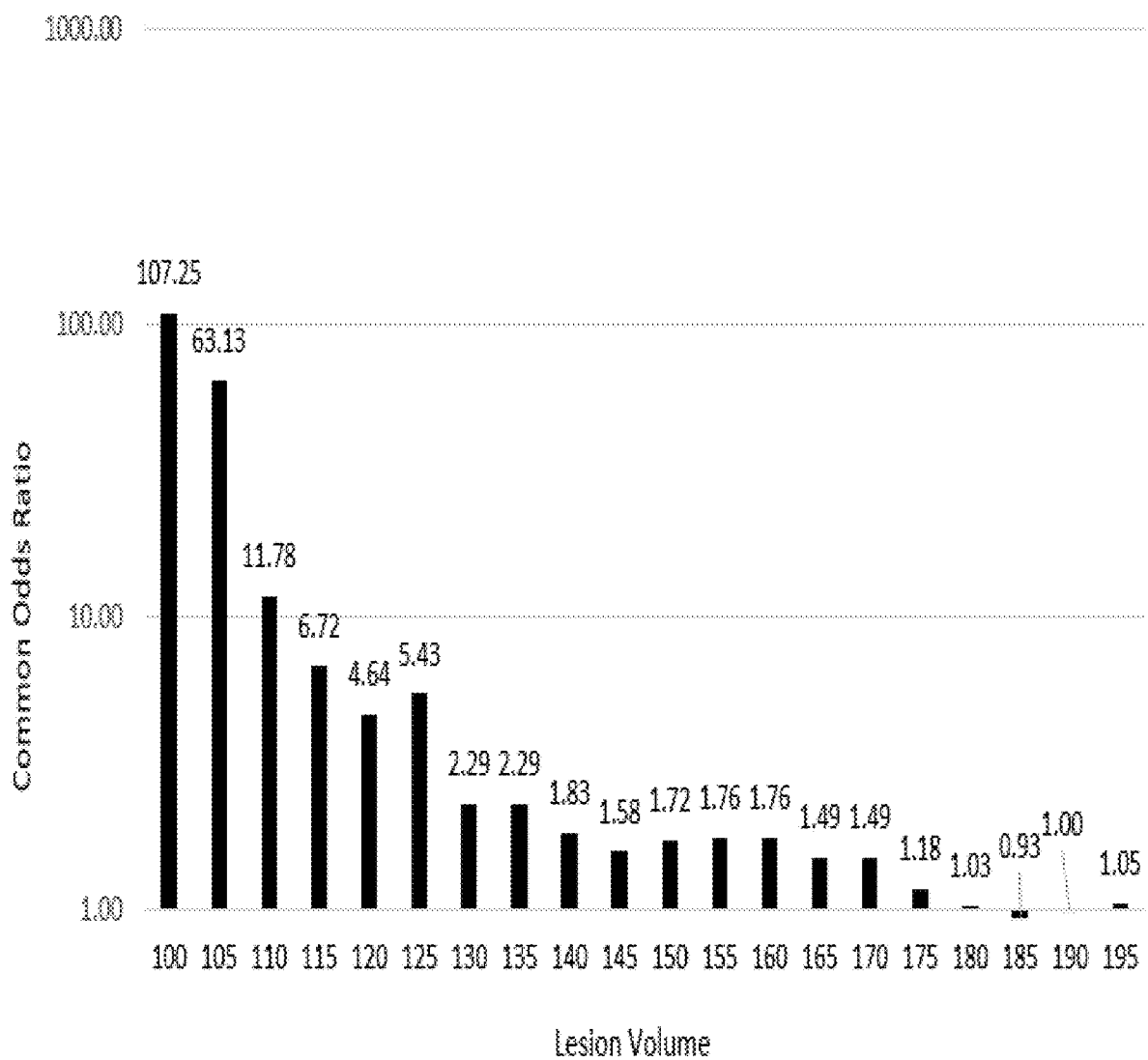

METHODS OF TREATING ISCHEMIC STROKE AT RISK FOR CEREBRAL OR CEREBELLAR EDEMA

CROSS-REFERENCE TO RELATED APPLICATIONS

This application is a continuation of U.S. application Ser. No. 18/734,541, filed Jun. 5, 2024, which claims priority benefit of U.S. Provisional application No. 63/637,163, filed Apr. 22, 2024, and U.S. Provisional application No. 63/642,492, filed May 3, 2024, and U.S. Provisional application No. 63/644,658, filed May 9, 2024, the disclosures of which are incorporated herein by reference in their entireties.

BACKGROUND

Following a large ischemic stroke, subjects can suffer from space-occupying brain edema (swelling). Life threatening cerebral swelling occurs in up to 8% of all hospitalized ischemic stroke patients and up to 15% of all middle cerebral artery stroke patients, for example. Such brain swelling (a.k.a. edema) presents itself, usually, a few days after the stroke and generally peaks on the 2nd or 3rd day.

Brain swelling increases intracranial pressure and can prevent blood from flowing to the brain, thereby depriving the brain of oxygen. Brain swelling can also block the exit routes of the brain and prevent fluids from leaving the brain. Moreover, as intracranial pressure builds within the skull, formerly healthy brain tissue is destroyed and transtentorial or uncal herniation can occur. Swelling within and around the brain can also cause morbidity and brain death, as well as secondary neurological disorders and the death of the subject.

Brain swelling can be associated with two separate molecular and physiological processes, namely cellular swelling of the neurons and astrocytes, and the transcapillary influx of ions and fluids to the site of the injury. Cellular swelling of the neurons and astrocytes occurs as a result of ion gradient changes between the cells and the extracellular space. One ion channel that is associated with cellular swelling is the $NC_{CA-ATP}$ channel, also known as the SUR1-TRPM4 channel. This channel is a non-selective $Ca^{2+}$ activated ATP sensitive cation channel that is activated when neuronal cells are depleted of intracellular ATP. The $NC_{CA-ATP}$ channel is believed to be composed of regulatory subunits, including a sulfonylurea type receptor 1 (SUR1) and a pore subunit related to transient receptor potential cation channel subfamily M member 4 (TRPM4).

Minimizing the extent of brain swelling is a major concern of physicians when treating subjects that suffer from conditions or diseases where brain edema can occur. However, treating brain edema is particularly difficult because of the prolonged time periods associated with swelling, the brain's overall functioning, and the placement of the brain within the skull. Wake-up stroke is an ischemic stroke that is first associated with neurological symptoms on awakening. Thus, the patient's last-known-well time corresponds to the onset of sleep on the evening before presentation. Given the uncertainty of when the stroke occurs, these patients are often ineligible for certain interventions, like tPA and other thrombolytics that have narrow windows when they can be used without excess harm. Hence, there is an urgent need for treatments that can be applied to the wake-up stroke population. Further, usage of mechanical thrombectomy in patients with large vessel occlusions has been low in part because of the fear that rapid reperfusion of such a large territory would cause hemorrhage or other adverse effects. Therefore, providing treatments that reduce the extent of brain edema would be advancement in the art.

SUMMARY

Embodiments of the invention include methods of improving outcomes in a patient diagnosed with an ischemic stroke using a SUR1-TRPM4 channel inhibitor in combination with mechanical thrombectomy. Patients may have a lesion volume of less than 140 $cm^3$ or less than 125 $cm^3$ and greater than 50 $cm^3$. The lesion volume may be measured by diffusion weighted imaging (DWI) or computerized tomography perfusion (CTP) imagining. Embodiments of the invention comprise administering a therapeutically effective amount of a SUR1-TRPM4 channel inhibitor to the subject. The SUR1-TRPM4 inhibitor may be administered via at least one continuous infusion, resulting in cumulative treatment time of at least 72 hours. The SUR1-TRPM4 channel inhibitor may be glibenclamide. The treatment may begin within 10 hours or the first stroke symptom.

In some embodiments, the minimum lesion volume may be 85 $cm^3$ and in others the maximum lesion volume may be 180 $cm^3$. In some embodiments, the maximum lesion volume may be 125 $cm^3$. The patient may be 18-70 years of age at the time treatment begins. The patient may have undergone thrombectomy prior to treatment or treatment may begin prior to thrombectomy or while the patient is undergoing thrombectomy. The patient may have a decompressive craniectomy before, during or after treatment. In other embodiments, the patient has experienced a wake-up stroke. In certain aspects involving wake-up stroke, the treatment begins within 10 hours of the midpoint between sleep onset (or last known to be normal) and time of waking.

Other embodiments may involve administering one or more continuous infusions for at least 72 hours, 96 hours, at least 120 hours or 168 hours. A bolus injection may be administered before any first continuous infusion. Certain embodiments may involve two or more continuous infusion dosages, wherein a first continuous infusion dosage is higher than a second continuous infusion dosage. Some embodiments contemplate a bolus dose administration and two or more continuous infusion dosages, wherein a first continuous infusion dosage is higher than a second continuous infusion dosage.

Exemplary SUR1-TRPM4 channel inhibitors include glibenclamide (also known as glyburide), 4-trans-hydroxy-glibenclamide, 3-cis-hydroxyglibenclamide, tolbutamide, chlorpropamide, tolazamide, repaglinide, nateglinide, meglitinide, midaglizole, gliquidone, LY397364, LY389382, gliclazide, glimepiride, metabolites that interact with SUR1, and combinations thereof.

In one aspect, the present disclosure includes methods of administering a formulation comprising: glyburide or a pharmaceutically acceptable salt thereof; a buffering agent; a base; and a sugar alcohol, wherein the formulation has a pH outside of the buffering capacity of the buffering agent. In some aspects, the formulation is free of cyclodextrin(s). In one aspect, wherein the formulation has a pH outside of the buffering capacity of the buffering agent, and wherein the buffering agent has a pKa of 7.7 to 9.2.

In one aspect, the present disclosure includes methods of administering an infusion solution comprising 500 ml saline solution, 3 to 5 mg glyburide, 100-140 mg mannitol, 10-12 mg Tris, and pH 7.8 to 9.

In one aspect, the present disclosure includes methods of administering a solution comprising 10-30 ml WFI, 3 to 5 mg glyburide, 100-140 mg mannitol, 10-12 mg Tris, and pH 9 to 11, e.g., 9.4 to 10.

In one aspect, the present disclosure includes a method of making and administering a glyburide formulation that has less than 1 wt. % loss of glyburide concentration (w/v) due to sorption to a polymeric container over the course of an infusion period comprising combining glyburide with a buffering agent having a pKa of 7.7 to 9.2, a sugar alcohol, and a base having a pKb of 0.1 to 1.5 in a molar ratio between the base and the glyburide of 5.0 to 6.7:1.

In some aspects, the present disclosure includes reconstitution the formulations of the present disclosure in a suitable diluent, e.g., saline or water for injection (WFI) such that the reconstituted formulation has a concentration of 4 to 60 mM, 5 to 50 mM, 6 to 40 mM, 7 to 30 mM, 8 to 25 mM, 9 to 23 mM, 10 to 21 mM, 11 mM, 12 mM, 13 mM, 14 mM, 15 mM, 16 mM, 17 mM, 18 mM, 19 mM, or 20 mM of the buffering agent.

In some aspects, the present disclosure includes diluting the formulations of the present disclosure in a saline solution, wherein the formulation has a pH of 7.8 to 9.

In some aspects, the present disclosure includes diluting the formulation in a saline solution, wherein the formulation has a pH that does not vary by more than 0.2 pH units during an infusion period of at least 24 hours.

In some aspects, the present disclosure includes formulations and methods having high storage stability, e.g., storage stability properties such that, upon storage for 6 months at 25° C./60% RH, has less than 0.2% degradation products, upon storage for 6 months at 40° C./75% RH, has less than 0.4% degradation products, and/or upon storage for 7 days at 70° C./75% RH, has less than 1.0% degradation products.

In some aspects, the present disclosure includes a method of increasing the solubility of a glyburide formulation in a saline infusion solution, comprising combining glyburide or a pharmaceutically acceptable salt thereof with: a buffering agent; a base; and a sugar alcohol, wherein the formulation has a pH outside of the buffering capacity of the buffering agent at 4° C., 20° C., or 25° C., to form a solubilized glyburide formulation having a glyburide solubility of 15 µg/ml in said saline infusion solution, wherein the glyburide formulation in the saline infusion solution has a pH of 7.8 to 9.

In some aspects, the present disclosure includes a method of minimizing the volume of saline infusion solution necessary for infusing a glyburide formulation into a human for 24 hours, comprising combining 3 to 5 mg glyburide or a pharmaceutically acceptable salt thereof with a buffering agent; a base; and a sugar alcohol, wherein the formulation has a pH outside of the buffering capacity of the buffering agent, wherein the glyburide formulation in the saline infusion solution has a pH of 7.8 to 9, and wherein the volume of the saline infusion solution used to infuse 3 to 5 mg glyburide or a pharmaceutically acceptable salt thereof to the human is about 500 ml.

In some aspects, the present disclosure includes a method of increasing the storage stability of a glyburide formulation comprising combining glyburide or a pharmaceutically acceptable salt thereof with a buffering agent; a base; and a sugar alcohol, wherein the formulation has a pH outside of the buffering capacity of the buffering agent, to form a stabilized glibenclamide formulation, wherein said stabilized glibenclamide formulation, after storage for at least 6 months at 25° C./60% RH, and has less than 0.2% degradation products upon storage for 6 months at 25° C./60% RH.

The disclosures of U.S. 2022/0280537 are incorporated herein by reference in their entireties for all purposes.

BRIEF DESCRIPTION OF THE DRAWING

FIG. 1 shows the clinical effects of a combination of administering glyburide with mechanical thrombectomy in human subjects.

DETAILED DESCRIPTION

The invention is based on several surprising observations. One such observation is that when patients diagnosed with an ischemic stroke involving occlusion of a large blood vessel are treated with a SUR1-TRPM4 inhibitor, the drug effect diminishes as a function of lesion volume, with the effect reducing to zero at about 140 cm$^3$. In order to observe this effect, an outcome that leaves a patient alive, yet bedridden, incontinent and wholly dependent on care is considered an undesirable outcome and the data must be analyzed in that manner. This concept comes from the development of a class of drugs called the lazaroids, with the outcome of saving lives, but leaving patients in such a debilitated state that it is considered a "fate worse than death." Thus, in the case of the modified Rankin Scale (the principal functional rating in stroke studies), a score of 5 (severely disabled) is considered a bad outcome, along with mortality. In this way, any effect that represents "mere" lifesaving, is discounted, ensuring that any drug effect provides a truly meaningful benefit to the patient. An analysis that includes a reduction in mortality (mRS 6) with a concomitant increase in severe disability (mRS 5) skews this reality and is not acceptable to the FDA or other regulatory authorities because it would mean saving a life only to provide no meaningful quality of life and a massive emotional and financial burden on the patient's family.

The other observation is that a SUR1-TRPM4 inhibitor can improve outcomes in patients with large vessel occlusions who undergo mechanical thrombectomy to remove the clot. Until recently such patients were excluded from mechanical thrombectomy because of the fear that rapid reperfusion of such a large territory would cause hemorrhage or other adverse effects. As thrombectomy began to be used in these patients successfully, it was entirely unclear whether these patients were still at risk of development edema and, thus, would benefit or be harmed by the additional treatment with a SUR1-TRPM4 inhibitor. Surprisingly, the combination of mechanical thrombectomy and SUR1-TRPM4 inhibitor provides vastly superior results.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In one embodiment, a method of improving outcomes in a subject following an ischemic stroke is presented. The stroke may be a large stroke, involving occlusion of a large cerebral or cerebellar vessel. Such a patient may be at risk to develop cerebral or cerebellar edema. In the case of the case of a cerebral stroke, it may involve infarction of the internal carotid artery (ICA) and/or one or more (usually proximal) segments of the middle cerebral artery (MCA). In the case of a cerebellar stroke, it may involve infarction of the posterior inferior cerebellar artery (PICA) or the superior cerebellar artery (SCA). The stroke may be a large hemispheric infarction (LHI) or a large cerebellar infarction (LCI). The stroke may be of at least moderate severity according to the NIH Stroke Scale (NIHSS).

The large strokes contemplated for treatment are associated with large ischemic lesions that may occupy at least about one-third of either the MCA or cerebellar territory, in the case of LHI and LCI, respectively. LHI has been variously defined as having a minimum lesion volume exceeding 50 $cm^3$ or 60 $cm^3$, but more typically is defined as a minimum lesion volume of 70-80 $cm^3$.

Magnetic Resonance Imaging Diffusion Weighted Imaging ("MRI DWI" or simply "DWI" or "MRI") is considered the "gold standard" in assessing lesion size. A threshold lesion size of 82 $cm^3$ by MRI DWI with 98% specificity for predicting late neurological deterioration associated with cerebral edema in LHI. This threshold accords well with the threshold more casually identified by other groups of 70-80 $cm^3$. Computed Tomography Perfusion (CTP) can similarly be used to accurately identify lesion volume.

It has surprisingly been discovered that the treatment effect of the SUR1-TRPM4 agent glyburide (also known as glibenclamide), as measured using the Modified Rankin Scale (mRS) diminishes to the "no effect" level at approximately 140 $cm^3$, with a robust treatment effect being seen at approximately 125 $cm^3$ and below, with the treatment effect in the LHI population increasing with smaller lesion volume. In this case, mRS scores of 5 and 6 are combined for analysis, meaning that severe disability is not considered a good outcome and, thus, provides no statistical power in demonstrating the drug works. Thus, the ideally treatable LHI patient has a minimum lesion volume of 50 $cm^3$ to 60 $cm^3$, but may also have a minimum lesion volume of 70 $cm^3$. It has also surprisingly been discovered that the treatment effect of the SUR1-TRPM4 agent glyburide in combination with mechanical thrombectomy extends the level of beneficial effect up to 180 $cm^3$. Thus, in some aspects, a LHI patient with a lesion volume of up to 180 $cm^3$ is treated according to the methods of the present disclosure to obtain a beneficial effect.

Stroke patients are routinely evaluated using non-contrast computed tomography (NCCT) and may be assigned an Alberta Stroke Program Early CT (ASPECTS) score. This score is a 10-point quantitative topographic CT scan score which is used to systematically examine CT scans of the brain to identify early signs of ischemia; a score of 1 is given for a normal region and 0 for a region showing signs of ischemia. The lower the score, the more progressive the ischemic change (i.e., the worse the stroke is considered to be). ASPECTS is determined from evaluation of two standardized regions of the MCA territory; the basal ganglia level and the supraganglionic level. Involvement of greater than ⅓ of the MCA territory at CT indicates early ischemic involvement of 2 or more different lobes of the cerebral hemisphere and basal ganglia, plus the insular cortex.

Patients undergoing treatment with a SUR1-TRPM4 inhibitor according to the methods of the present disclosure are selected for thrombectomy. A patient is generally "selected for thrombectomy" using one or more imaging modalities. Non-contrast CT is almost always used as it can identify hemorrhage and can be used to generate an ASPECTS score. Hemorrhage or an ASPECTS score≤2 would generally preclude a patient from being selected for thrombectomy. In addition, some form of angiography is typically employed, CT angiography or MR angiography, in order to confirm that the patient has a blockage that can be removed using thrombectomy. Recanalized patients, either spontaneously or using thrombolytics like tPA, would not be selected for thrombectomy. While the occlusion of a large vessel, such as the ICA or one of the proximal branches of the MCA and/or the presence of a large lesion (≥70 $cm^3$ or ASPECTS≤5) formerly precluded thrombectomy, this is no longer the case and these patients are increasingly selected for thrombectomy, though other factors, such time from stroke onset and other risk factors become more important. It is more critical in such patients to be selected for thrombectomy as soon as possible after the stroke onset. A patient may also undergo CT perfusion or MRI as part of the selection process, and may have a quantitative lesion volume measurement as a result. The exact method a physician uses to select a patient for thrombectomy will depend on medical judgment rendered based on the specific presentation of the patient, including all risk factors and whether the patient is likely to benefit from thrombectomy. This is routinely done and well within the skill of the ordinary skill in stroke treatment. In accordance with the invention, any patient who is selected for thrombectomy must actually receive a thrombectomy. In other words, this aspect of the invention contemplates that a patient receives both a thrombectomy and treatment with a SUR1-TRPM4 inhibitor, but that these two interventions may be done in either order sequentially or simultaneously.

Treatment of patients with a SUR1-TRPM4 inhibitor selected to undergo a thrombectomy may be initiated before, during or after a thrombectomy. If treatment begins after thrombectomy, the patient may have a non-contrast CT to confirm the absence of hemorrhage prior to beginning treatment. A patient may also undergo CT perfusion or MRI after the thrombectomy to determine lesion volume prior to treatment.

Treated patients selected for thrombectomy will typically have a maximum ischemic lesion volume of 180 $cm^3$ and may have a maximum lesion volume of 170, 160, 150, 140, 130, 125, or 120 $cm^3$ at the time treatment with the SUR1-TRPM4 inhibitor begins. The lesion volume is best ascertained using CTP or MRI. Lesion volume may be ascertained before or after thrombectomy. If before thrombectomy, the physician should have a reasonable expectation that the maximum lesion volume is not exceeded during the thrombectomy procedure. Thus, the maximum lesion volume determined prior to thrombectomy should generally be smaller than the maximum to allow for lesion expansion over the time it takes to do a thrombectomy. Thus, the maximum lesion volume determined prior to thrombectomy may be 10%, 20%, 30% or even 40% smaller than the maximum lesion volume determined after the thrombectomy, depending on how quickly the procedure can be conducted.

Treatment of patients experiencing a "wake-up" stroke is specifically contemplated. Wake-up strokes occur when a patient goes to bed without stroke symptoms, but upon awakening has symptoms. It is considered likely that the stroke occurred as the patient woke up and so any time-limitations on treatment may be measured from the time of awakening or some earlier time point between the time of going to sleep and the time of awakening.

The method comprises administering one or more continuous infusions of a SUR1-TRPM4 channel inhibitor to the subject in a patient that undergoes mechanical thrombectomy. The infusion may continue cumulatively for at least about 72 hours after starting the continuous infusion(s). It has been found that administering the SUR1-TRPM4 channel inhibitor can reduce the incident of late neurological deterioration or death, thereby improving outcomes, as measured by conventional scales use to assess stroke.

Patients with ischemic stroke may be considered for treatment when the subject exhibits at least one factor selected from the group consisting of: a National Institutes of Health Stroke Scale (NIHSS) score of at least 10; a Alberta Stroke Program Early CT Score (ASPECTS) of 7 or less; ASPECTS of 4 or less; a MRI DWI lesion volume of greater than 70 $cm^3$; a MRI DWI lesion volume of greater than 82 $cm^3$; a CT perfusion core that is greater than 50 $cm^3$; a CT perfusion core that is greater than 70 $cm^3$; poor collateral circulation determined by CT angiography (or other means); a CT scan that shows a hypodensity covering at least 33% of the middle cerebral artery territory; and/or a CT scan that shows a hypodensity covering at least 50% of the middle cerebral artery territory. In some embodiments, the subject is first assessed to have an NIHSS of 10 or greater, and then assessed by one of the other methods outlined above. In some embodiments, the subject is first assessed to have an NIHSS of 10-20, and then assessed by one of the other methods outlined above.

In some embodiments, the subject is treated when the ASPECTS score is ≤5, ≤4, ≤3, or ≤2. In some embodiments the subject is treated when the MRI DWI lesion volume is greater than 82 $cm^3$.

In particular, patients suffering from a Large Hemispheric Infarction are especially at risk of brain swelling and treatable according to the invention. These subjects typically have a middle cerebral artery territory stroke and can be further identified radiologically using MRI DWI or CT perfusion of at least about 70 $cm^3$, at least about 80 $cm^3$, or an ASPECTS score of ≤5, ≤4, ≤3, or ≤2. In methods contemplated herein of treating subjects with LHI, it is preferred that subjects are ≤about 75 years old and most preferably ≤about 70 years old. It is also preferred that subjects have an NIHSS≥10 and that drug is administered in ≤10 hours from the index stroke or time last known well, but most preferably within ≤9 hours. In some embodiments, the subject has NIHSS of 10-20. These methods will result in improvements on one or more clinically relevant endpoints on the modified Rankin Scale (as a full ordinal scale and/or dichotomized), but collapsing mRS 5 and 6 to avoid the aforementioned lazaroid problem. These improvements will manifest at one or more time points to include about 90 days, about 180 days/6 months and about 12 months following the stroke.

Related to the methods of treating large strokes, methods of testing a drug to treat large strokes are also contemplated. According to these methods patients ages 18 and older are selected radiologically, as described above, and enrolled. Subjects preferably have an NIHSS of ≥10, e.g., 10, 11, 12, 13, 14, 15, 16, 17, 18, 19, 20, or any score between 10-20, e.g., ≥10 and ≤16, ≤17≤18, ≤19, ≤20, and are treated with a SUR1-TRPM4 channel inhibitor, or matching placebo, beginning within ≤about 10 hours of the stroke (or time last known well), more preferably ≤9 hours, with treatment lasting for up to about 72 hours. These methods will result in improvements in the drug versus placebo groups on one or more clinically relevant endpoints, including: survival/mortality, the modified Rankin Scale (as a full ordinal scale and/or dichotomized), collapsing mRS 5 and 6. These assessments are made at one or more time points to include about 90 days, about 180 days/6 months and about 12 months following the stroke.

In assessing the outcome, mRS is preferably analyzed using an analysis that retains the ordinal scale, such as the Mann Whitney test (and similar tests), ordinal logistic regression under a proportional odds assumption, a sliding dichotomy. Success is defined in terms of a two-sided p-value of <0.05 or an odds ratio where the 90% confidence interval does not cross 1. An odds ratio so calculated should preferably be >1 and generally >1.1 and more preferably >1.2 and most preferably >1.3 in favor of drug.

SUR1-TRPM4 Channel Inhibitors

SUR1-TRPM4 channel inhibitors can include any active agent that is effective for inhibiting SUR1-TRPM4, and some examples can include glyburide (also known as glibenclamide), 4-trans-hydroxy-glibenclamide, 3-cis-hydroxyglibenclamide, tolbutamide, chlorpropamide, tolazamide, repaglinide, nateglinide, meglitinide, midaglizole, gliquidone, LY397364, LY389382, gliclazide, or glimepiride, metabolites that interact with SUR1, pharmaceutically acceptable salts thereof, or combinations thereof. Some compounds that act on non-selective channels that may be associated with SURs include, for example, pinkolant, flufenamic acid, mefenamic acid, niflumic acid, rimonabant, and SKF 9635. In one embodiment, the SUR1-TRMP4 channel inhibitor is glyburide or a pharmaceutically acceptable salt thereof. In another embodiment, the SUR1-TRMP4 channel inhibitor is tolbutamide or a pharmaceutically acceptable salt thereof. In yet another embodiment, the SUR1-TRMP4 channel inhibitor is gliclazide or a pharmaceutically acceptable salt thereof.

Dosage and Administration

The SUR1-TRPM4 channel inhibitor can be administered as a bolus injection, a continuous infusion, or a combination thereof. In some instances, the administration can include multiple bolus injections or multiple continuous infusions. In other embodiments, the administration can comprise one or more continuous infusion after a bolus injection. For example, a bolus injection can be given, followed by a first continuous infusion, followed by a second continuous infusion of a lower infusion rate compared to the first infusion. In another embodiment, a bolus injection is followed by a continuous infusion. In another embodiment, a first continuous infusion is followed by a bolus injection and then by a second continuous infusion. In yet another embodiment, a first continuous infusion is followed by a second continuous infusion, and a third continuous infusion.

The administration presented herein can occur over prolonged time periods. The administration can occur for ≥12 hours, ≥24 hours, ≥48 hours, ≥72 hours, ≥76 hours, ≥80 hours, >84 hours, >88 hours, >92 hours, >96 hours, ≥100 hours, ≥104 hours, ≥108 hours, ≥112 hours, ≥116 hours, ≥120 hours, ≥124 hours, ≥128 hours, ≥132 hours, ≥136 hours, >140 hours, ≥144 hours, ≥148 hours, ≥152 hours, ≥156 hours, ≥160 hours, ≥164 hours, ≥168 hours, or >172 hours. In one embodiment, the administration comprises one or more continuous infusion for cumulative length of time of at least 72 hours. In another embodiment, the administration comprises one or more continuous infusion for at least 96 hours. In yet another embodiment, the administration comprises one or more continuous infusion for at least 120 hours. In alternative examples, the administration of the one or more continuous infusions can occur for ≤72 hours, ≤48 hours, or ≤24 hours.

The exact dosage will vary based on the underlying condition, the extent of swelling, the subject's body weight, and/or the SUR1-TRMP4 channel inhibitor that is administered. Bolus injections are anticipated to be administered from about 100 μg to about 200 μg. In one embodiment, the bolus injection is from about 110 µg to about 140 µg, or about 125 µg. In another embodiment, the bolus injection is from about 140 µg to about 160 µg, or about 150 µg. In yet another embodiment, the bolus injection is from about 160 µg to about 190 µg, or about 175 µg. Continuous infusions are anticipated to be administration at an infusion rate from about 100 µg/hr to about 300 µg/hr. In one 5 embodiment, the infusion rate is from about 110 µg/hr to about 140 µg/hr, or about 125 µg/hr. In another embodiment, the infusion rate is from about 140 µg/hr to about 160 µg/hr, or about 150 µg/hr. In yet another embodiment, the infusion rate is from about 160 µg/hr to about 190 µg/hr, or about 175 µg/hr. In further embodiments, the infusion rate is from about 190 µg/hr to about 225 µg/hr, or about 200 µg/hr. Additional embodiments include an infusion rate from about 225 µg/hr to about 300 µg/hr, or about 250 µg/hr.

In some aspects, the present disclosure includes any of the following exemplary items:

1. A method of improving outcomes in a patient diagnosed with an ischemic stroke wherein the patient has experienced a wake-up stroke, comprising administering a SUR1-TRPM4 channel inhibitor to the patient.
2. The method of item 1, wherein the patient is 18-70 years of age at the time treatment begins.
3. The method of item 1 or item 2, wherein the patient has undergone mechanical thrombectomy before the administering step.
4. The method of item 3, wherein the administering begins prior to or during the mechanical thrombectomy.
5. The method of any one of items 1-4, wherein treatment begins within 9 hours of the midpoint between sleep onset (or last known to be normal) and time of waking.
6. The method of item 1, wherein the treatment begins within 10 hours of the midpoint between sleep onset (or last known to be normal) and time of waking.
7. The method of any one of items 1-6, wherein the administering begins within 8 hours of the first stroke symptom.
8. The method of any one of items 1-7, wherein the SUR1-TRPM4 inhibitor is administered in one or more continuous infusions with a total duration of at least 72 hours.
9. The method of any one of items 1-8, wherein the patient undergoes a decompressive craniectomy.
10. The method of any one of items 1-9, wherein the patient has a lesion volume of 180 cm$^3$ or less.
11. The method of any one of items 1-9, wherein the patient has a lesion volume less than 180, 170, 160, 150, 140, 130, 125, 120, 110, 100, 90, or 80 cm$^3$.
12. The method of any one of items 1-9, wherein the patient has a lesion volume of >50 cm$^3$ and <125 cm$^3$ or >50 cm$^3$ and <100 cm$^3$.
13. The method of any one of items 1-12, wherein the SUR1-TRPM4 channel inhibitor comprises a member selected from the group consisting of glibenclamide, 4-trans-hydroxy-glibenclamide, 3-cis-hydroxyglibenclamide, tolbutamide, chlorpropamide, tolazamide, repaglinide, nateglinide, meglitinide, midaglizole, gliquidone, LY397364, LY389382, gliclazide, glimepiride, a pharmaceutically acceptable salt thereof, a metabolite thereof that interacts with SUR1, and a combination thereof.
14. The method of any one of items 1-13, the SUR1-TRPM4 channel inhibitor is glibenclamide.
15. A method of treating ischemic stroke in a patient that has experienced a wake-up stroke, comprising treating the patient with a therapeutically effective amount of a SUR1-TRPM4 inhibitor.
16. The method of item 15, wherein treatment begins prior to a mechanical thrombectomy.
17. The method of item 15, wherein treatment begins during or after a mechanical thrombectomy.
18. The method of any one of items 15-17, wherein the patient has a lesion volume less than 180, 170, 160, 150, 140, 130, 125, 120, 110, 100, 90, or 80 cm$^3$.
19. The method according to any of items 1-18, wherein the patient is selected to undergo mechanical thrombectomy using non-contrast computed tomography.
20. The method of any one of items 1-18, wherein the patient is treated with a tissue plasminogen activator.
21. The method according to item 20, wherein the patient has an ASPECTS score ≤7.
22. The method according to any of items 15-21, wherein the patient is selected to undergo mechanical thrombectomy using computed tomography perfusion or magnetic resonance imaging.
23. The method according to any of items 18-22, wherein the lesion volume is measured by using computed tomography perfusion or magnetic resonance imaging.
24. The method according to any of items 17-23, wherein the patient undergoes a non-contrast computed tomography after mechanical thrombectomy, but before treatment with the SUR1-TRPM4 inhibitor begins.
25. The method according to any of items 17-23, wherein the lesion volume is determined prior to mechanical thrombectomy.
26. The method according to any of items 17-23, wherein the lesion volume is determined after mechanical thrombectomy.
27. The method according to any of items 1-26, wherein the patient has a NIH Stroke Scale (NIHSS) score of 10 to 20.
28. The method according to any of items 1-26, wherein the patient has a NIH Stroke Scale (NIHSS) score of 10 to 18.
29. The method according to any of items 1-26, wherein the SUR1-TRPM4 channel inhibitor is glyburide or a pharmaceutically acceptable salt thereof in a formulation comprising a buffering agent, a base, and a sugar alcohol, wherein the formulation has a pH outside of the buffering capacity of the buffering agent, and wherein the buffering agent has a pKa of 7.7 to 9.2.
30. The method of any preceding item, wherein the pharmaceutically acceptable salt thereof is a sodium addition salt.
31. The method of any preceding item, wherein the glyburide or pharmaceutically acceptable salt thereof is about 2.7 to 3.1% (w/w) of the formulation.
32. The method of any preceding item, wherein the sugar alcohol is about 84 to 90% w/w of the formulation.
33. The method of any preceding item, comprising the sugar alcohol and the glyburide or pharmaceutically acceptable salt thereof in a weight ratio of 28 to 35:1.
34. The method of any preceding item, wherein, upon storage for 12 months at 25° C./60% relative humidity (RH), has a pH that is within about 0.2 pH unit of the formulation prior to storage, or wherein, upon storage for 6 months at 40° C./75% RH, has a pH that is within about 0.2 pH unit of the formulation prior to storage, or wherein, upon storage for 4 weeks at 70° C./75% RH, has a pH that is within about 0.2 pH unit of the formulation prior to storage.
35. The method of any preceding item, wherein the buffering agent is a buffer having a pH of 7.8 to 9.

36. The method of any preceding item, wherein the formulation comprises the base and the glyburide or pharmaceutically acceptable salt thereof in a ratio so the formulation has a pH of 10.1 to 10.9 when reconstituted in water for injection (WFI).
37. The method of any preceding item, wherein the formulation comprises the sugar alcohol and the glyburide or pharmaceutically acceptable salt thereof in a weight ratio of 27 to 40:1.
38. The method of any preceding item, wherein the formulation comprises the sugar alcohol and the buffering agent in a weight ratio of 8 to 12:1.
39. The method of any preceding item, wherein the formulation comprises 26 to 34 mg/ml of the sugar alcohol.
40. The method of any preceding item, wherein the base and the glyburide or pharmaceutically acceptable salt thereof have a molar ratio of 5.4 to 6.3:1 in the formulation.
41. The method of any preceding item, wherein the formulation comprises about 8 to 12% (w/w) of the buffering agent.
42. The method of any preceding item, wherein the formulation is free of cyclodextrins.
43. A method of any of items 1-29, wherein the formulation comprises:
    a) glyburide or a pharmaceutically acceptable salt thereof;
    b) a buffering agent;
    c) a base; and
    d) a sugar alcohol,
    wherein the formulation has a pH outside of the buffering capacity of the buffering agent, and
    wherein the formulation is free of cyclodextrins.
44. The method of item 43, wherein the glyburide or pharmaceutically acceptable salt thereof is about 2.7 to 3.1% (w/w) of the formulation, and/or wherein the sugar alcohol is about 84 to 90% (w/w) of the formulation.
45. The method of item 43, comprising the sugar alcohol and the glyburide or pharmaceutically acceptable salt thereof in a weight ratio of 28 to 35:1.
46. The method of item 43, wherein, upon storage for 12 months at 25° C./60% relative humidity (RH), has a pH that is within about 0.2 pH unit of the formulation prior to storage, or wherein, upon storage for 6 months at 40° C./75% RH, has a pH that is within about 0.2 pH unit of the formulation prior to storage, or wherein, upon storage for 4 weeks at 70° C./75% RH, has a pH that is within about 0.2 pH unit of the formulation prior to storage.
47. The method of item 43, wherein the buffering agent is a buffer having a pH of 7.8 to 9.
48. The method of item 43, comprising the base and the glyburide or pharmaceutically acceptable salt thereof in a ratio so the formulation has a pH of 10.1 to 10.9 when reconstituted in water for injection (WFI).
49. The method of item 43, wherein the formulation comprises the sugar alcohol and the glyburide or pharmaceutically acceptable salt thereof in a weight ratio of 27 to 40:1.
50. The method of item 43, wherein the formulation comprises the sugar alcohol and the buffering agent in a weight ratio of 8 to 12:1.
51. The method of item 43, wherein the formulation comprises 26 to 34 mg/ml of the sugar alcohol.
52. The method of item 43, wherein the base and the glyburide or pharmaceutically acceptable salt thereof have a molar ratio of 5.4 to 6.3:1.
53. The method of item 43, wherein the formulation comprises about 8 to 12% (w/w) of the buffering agent, and wherein the buffering agent has a pKa of 7.7 to 9.2.

Formulations

The methods and formulations provided herein provide pharmaceutically acceptable glyburide formulations, including concentrated solutions, diluted solutions, and lyophilized formulations, that solve the sorption, degradation, instability, and low solubility problems associated with prior art pharmaceutical formulations glyburide.

Examples of suitable pharmaceutically acceptable diluents such as WFI (water for injection) and solutions containing isotonic saline are known in the art. Pharmaceutically acceptable aqueous solutions include Ringer's solution, Hartmann's solution, 0.9% saline, 0.45% N saline, WFI (water for injection), D5W (5% dextrose in water), phosphate-buffered saline (PBS), and a dextrose/saline solution (D2.5W (i.e., 2.5% dextrose in water) and 0.45% N saline).

As used herein, "Ringer's solution" refers to a pharmaceutically acceptable buffered saline solution having sodium chloride, potassium chloride, and calcium chloride salts.

As used herein, "Hartmann's solution" refers to a lactated Ringer's solution. A typical Hartmann's solution includes 131 mM sodium, 5 mM potassium, 2 mM calcium, 11 mM chloride, and 29 mM lactate (sodium chloride 0.6%, sodium lactate 0.25%, potassium chloride 0.04%, calcium chloride 0.027%).

As used herein, pharmaceutically acceptable saline solution is a solution suitable for administration to a patient that includes water and sodium chloride, and may optionally contain buffers, preservatives, or other components, typically in small amounts. For example, pharmaceutically acceptable saline solutions include 0.9% saline (9 g NaCl in 100 ml distilled, filtered water, containing 150 mM sodium and 150 mM chloride) and saline solutions having 154 mM sodium and 154 mM chloride.

Generally herein, the term "or" includes "and/or."

As used herein, a plurality of compounds, elements, or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Furthermore, certain compositions, elements, excipients, ingredients, disorders, conditions, properties, steps, or the like may be discussed in the context of one specific embodiment or aspect or in a separate paragraph or section of this disclosure. It is understood that this is merely for convenience and brevity, and any such disclosure is equally applicable to and intended to be combined with any other embodiments or aspects found anywhere in the present disclosure and claims, which all form the application and claimed invention at the filing date. For example, a list of method steps, active agents, kits, or compositions described with respect to a formulation or method of treating a certain subject is intended to and does find direct support for embodiments related to compositions, formulations, and methods described in any other part of this disclosure, even if those method steps, active agents, kits, or compositions are not re-listed in the context or section of that embodiment or aspect.

The inventors have found that glyburide in conventional intravenous glyburide formulations readily and extensively binds to polymeric containers, e.g., containing polyvinyl chloride (PVC) and polyurethane (PUR) infusion sets. While use of low-sorbing polyethylene-lined infusion sets minimize the sorption, such specialized infusion sets are not practical for multiple reasons including that it is difficult to source such specialized infusion sets and intravenous glyburide is intended for use in an emergency-care setting and for indications where minimization in the time from the patient's last-know-normal to dosing is critical for efficacy (i.e. "time is brain"). Thus, presenting additional complexities in the handling and administration of intravenous glyburide, i.e., requiring strict use of specialized infusion components in emergency settings, would delay patient dosing and adversely affect patient outcome. Moreover, use of commonly used materials with prior art intravenous glyburide formulations would result in loss of significant amounts of the active pharmaceutical ingredient due to sorption, resulting in administration of an unknown and likely sub-therapeutic dose of the glyburide. In addition, use of commonly used materials with prior art intravenous glyburide formulations results in instability and degradation leading to unacceptable quality drug product. Further, it is unsafe to administer unknown amounts of glyburide or to attempt to increase the volume of drug to administer because administering glyburide in higher doses (e.g., at a rate greater than an average rate of 0.25 mg/hour (6 mg/day)) can result in hypoglycemia. Further, it is not desirable to implement flushing procedures, which can be complex, time-consuming, imprecise, wasteful, and risk contamination. Moreover, the inventors have found that glyburide in prior art intravenous glyburide formulations readily and extensively binds to all filter components (data not shown). Thus, it is necessary to provide new intravenous glyburide formulations that avoid binding to commonly used infusion sets and filter materials and allow healthcare providers to treat patients with a precise dose within the appropriate dosing window (as close to immediately after a stroke, infarction, injury, etc.) using commonly used medical supplies, while avoiding complication, avoiding wasted drug, and reducing the amount of infusion fluid administered to patients.

In a first aspect, the present disclosure provides a formulation containing a stable, therapeutic dose of glyburide that has less than 8, 7, 6, 5, 4, 3, 2, 1, 0.5, 0.2, 0.1, 0.05, 0.01% loss of glyburide concentration (w/v) due to sorption to a polymeric container, e.g., containing polyvinyl chloride (PVC), polyurethane (PUR), polypropylene, polyamide, polystyrene, polyethylene terephthalate (PET), polycarbonate (PC), acrylonitrile butadiene (ABS), polybutadiene, polyolefin, ethylene vinyl acetate, polyetheretherketone (PEEK), and mixtures, combinations, and copolymers thereof.

In a second aspect, the present disclosure provides a formulation containing a stable, therapeutic dose of glyburide that has less than 8, 7, 6, 5, 4, 3, 2, 1, 0.5, 0.2, 0.1, 0.05, 0.01% loss of glyburide concentration (w/v) due to sorption to in line filter materials.

In a third aspect, the present disclosure provides a method and formulation for controlling the pH of a glyburide solution in a narrow desired range both before and after dilution in an infusion fluid.

In a fourth aspect, the present disclosure provides a method and formulation for minimizing or avoiding degradation products from forming in a stored glyburide solution.

In a fifth aspect, the present disclosure provides a method and formulation for reducing the infusion rate, reducing drug wastage, and reducing saline intake into a subject being treated with intravenous glyburide.

In a sixth aspect, the present disclosure provides a method and formulation for maintaining a sufficiently high concentration of glyburide in solution during formulation compounding that can enable filling into appropriately-sized container to achieve the therapeutic dose, e.g., 3-5 mg per day glyburide.

In a seventh aspect, the present disclosure provides a method and formulation for providing sufficient solubility, stability, and desired pH upon reconstitution to achieve a desired high concentration during drug preparation.

In an eighth aspect, the present disclosure provides a method and formulation for providing sufficient solubility, stability, and desired pH upon further dilution of the reconstituted glyburide formulation into infusion fluids (e.g., in saline bags at a concentration of 6-10 μg/ml) for dosing over a 3, 4, 6, 12, 24, 30, 36, 48, 72, 96, or 120 hour period.

In one aspect, the method and formulation of the present disclosure includes compounding a glyburide formulation including glyburide, a buffering agent, and a base as specified herein. In one aspect, the buffering agent has a pKa of 7.7 to 9.2, 7.8 to 9.1, 7.9 to 9.0, 8.0 to 8.9, 8.05 to 8.8, 8.1 to 8.7, or any specific pKa in the specified ranges. For example, and without limiting the foregoing disclosure, the buffering agent may be a Tris, a lysine, an arginine, an ethylenediamine, an imidazole, a 4-(2-Hydroxyethyl) morpholine, a triethanolamine, a glucamine, a deanol (dimethylaminoethanol), phosphate, phosphate-buffered saline (PBS) or a combination thereof. In one aspect, the buffering agent of the present disclosure has buffering capacity in a pH range of 7 to 9. In one aspect the Tris may be a combination of Tris-HCl and Tris-base. In one aspect, the lysine is lysine-HCl. In one aspect, the arginine is arginine-HCl.

In one aspect, the present disclosure includes methods and formulations comprising glyburide, a buffering agent, a base, and a sugar alcohol, wherein the formulation has a pH outside of the buffering capacity of the buffering agent, and the formulation is suitable (including safe, in a sustained therapeutically effective amount, and tolerable) for infusion to a human for a period of 24 hours or more. In one aspect, the formulation (reconstituted formulation) has a pH of greater than 9.0, greater than 9.5, greater than 10.0, or greater than 10.5, e.g., 9.3 to 11, whereas the buffering agent has buffering capacity in a pH range of 7 to 9.

In some embodiments, the formulation is able to maintain a stable pH. For example, the formulation has a pH that is within about 0.1 or about 0.2 pH unit after storage at one, two, or four weeks, or 3 months, 6 months, or 12 months at or about 25° C./60% relative humidity (RH), 40° C./75% RH, or 70° C./75% RH. In some embodiments, the glyburide has increased stability as compared to the same formulation that either lacks a buffering agent or has a buffering agent that has a buffering capacity overlapping with the pH of the formulation. In some aspects, the stability can be determined by measuring generation of degradation products. For example, the degradation products can be measured by HPLC. In some aspects, the degradation products are quantified based on relative retention time (RRT) on HPLC.

In some aspects, the buffering agent is a combination of Tris-HCl and Tris-base. In some aspects the weight ratio between Tris-HCl and Tris-base is 7:4, 6.7:4.5, 6.5:4.7, 6.4:4.8, 6.3:4.9, 6.2:5.0, or 6.1:5.1.

In some aspects, a lyophilized glyburide formulation comprises about 5 to 15%, 6 to 14%, 7 to 13%, 8 to 12%, 9 to 13%, or 10 to 12% (w/w) of the buffering agent. In some aspects, a reconstituted glyburide formulation comprises about 5 to 15%, 6 to 14%, 7 to 13%, 8 to 12%, 9 to 13%, or 10 to 12% (w/w) of the buffering agent. In some aspects, a reconstituted glyburide formulation comprises about 1 to 100 mM, 2 to 80 mM, 3 to 70 mM, 4 to 60 mM, 5 to 50 mM, 6 to 40 mM, 7 to 30 mM, 8 to 25 mM, 9 to 23 mM, 10 to 21 mM, 11 mM, 12 mM, 13 mM, 14 mM, 15 mM, 16 mM, 17 mM, 18 mM, 19 mM, or 20 mM of the buffering agent. In some aspects, a reconstituted glyburide formulation comprises about 1 to 5 mg/ml, 1.2 to 4 mg/ml, 1.5 to 3.5 mg/ml, or 2 to 3 mg/ml of the buffering agent.

In some aspects, the buffering agent is a buffer having a pH of 7.8 to 9, 8.1 to 8.9, 8.2 to 8.8, 8.3 to 8.7, 8.4 to 8.6, or 8.5.

In some aspects, the present disclosure includes use of an admixture device that enables reconstitution and transfer of the lyophilized formulation between a vial and an IV bag prior to administration. The admixture device may be a needle-free device. The admixture device may meet the requirements of USP <797>. The admixture device may have a dual channel design providing dedicated fluid pathways into and out of the IV bag. In one aspect, the present disclosure includes use of an admixture device as described in U.S. Pat. No. 8,551,067 (Zinger), which is incorporated herein by reference in its entirety. In one aspect, the present disclosure includes use of an admixture device as described in U.S. Pat. No. 10,688,295 (Lev), which is incorporated herein by reference in its entirety. In some aspects, the present disclosure includes a method of using the VIAL2BAG®, VIAL2BAG ADVANCED™, and/or MIX2VIAL® admixture devices to reconstitute and transfer the lyophilized formulation between a vial and an IV bag prior to administration.

In a second aspect, the base is a strong base having a pKb of 0.1 to 1.5. Any pharmaceutically acceptable strong base may be used. For example, and without limiting the foregoing disclosure, the base may be NaOH, CaOH, or KOH.

In a third aspect, the formulation of the present disclosure includes a specific weight ratio between the glyburide and the base to achieve a pH target in a range of 9.8 to 11.2, 9.9 to 11.1, 10.0 to 11.0, 10.1 to 10.9, 10.2 to 10.8, 10.3 to 10.7, or 10.4 to 10.6, in the formulation.

In some aspects, the formulation of the present disclosure includes a specific molar ratio between the base and the glyburide is 5.0 to 6.7:1, 5.1 to 6.6:1, 5.2 to 6.5:1, 5.3 to 6.4:1, 5.4 to 6.3:1, 5.5 to 6.2:1, 5.6 to 6.1:1, 5.7 to 6.0:1, or 5.2:1, 5.3:1, 5.4:1, 5.5:1, or 5.6:1, in the formulation. The molar ratio used according to the present disclosure is unexpectedly about 2-fold higher than those used in prior art glyburide formulations.

In some aspects, the lyophilized glyburide formulation comprises about 2 to 3.5%, 2.5 to 3.3%, 2.7 to 3.1%, 2.8 to 2.98%, 2.9 to 2.97%, or 2.94 to 2.96% (w/w) of the glyburide.

In some aspects, the lyophilized glyburide formulation comprises about 70 to 93%, 75 to 92%, 80 to 91%, 84 to 90%, 86 to 89%, or 87 to 89% (w/w) of a sugar alcohol of the present disclosure. In some aspects, the sugar alcohol is mannitol, sorbitol, xylitol, or a combination thereof. In some aspects, the sugar alcohol is mannitol.

In some aspects, the formulation of the present disclosure includes a specific weight ratio between the sugar alcohol and the glyburide in the formulation. In some aspects, the formulation of the present disclosure includes a specific weight ratio between the sugar alcohol and the buffering agent is 5 to 15:1, 6 to 14:1, 7 to 13:1, 8 to 12:1, 9 to 11:1, 9.5:1, 10:1, or 10.5:1 in the formulation.

In some aspects, a reconstituted glyburide formulation comprises about 20 to 40 mg/ml, 24 to 36 mg/ml, 26 to 34 mg/ml, 38 to 32 mg/ml, 29 mg/ml, 30 mg/ml, or 31 mg/ml of the sugar alcohol.

In some aspects, a reconstituted glyburide formulation has a pH of about 9.3 to 11, 9.4 to 10.9, 9.5 to 10.8, 9.6 to 10.7, 9.7 to 10.6, 9.6 to 10.5, 9.7, 9.8, 9.9, 10.0, 10.1, 10.2, 10.3, or 10.4. In some aspects, a reconstituted glyburide formulation has a pH of 9.5 to 10.0.

In some aspects, the glyburide is a free acid or pharmaceutically acceptable salt thereof. In some aspects the glyburide formulation comprises a sodium addition salt of glyburide. As used throughout this disclosure, recitations of "glyburide" may also describe salts, esters, hydrates, solvates, racemates, tautomers, stereoisomers, and/or optically active forms thereof.

In some aspects, the present disclosure includes preparing aqueous solutions of glyburide in a buffer of the present disclosure in the concentrations described herein, adding a base of the present disclosure in the weight ratios to glyburide described herein, and freeze-drying the solution to provide a lyophilized solid composition. In some aspects the aqueous solution may further contain a sugar alcohol of the present disclosure in the concentrations described herein.

In some aspects, formulations of the present disclosure are free of one or more of cyclodextrin(s), meglumine, sugar(s) such as, e.g., fructose, mannose, galactose, arabinose, xylose and ribose, etc., and also oligosaccharides such as disaccharides (maltose, lactose, sucrose, trehalose, etc.) and trisaccharides (e.g. raffinose, maltotriose, etc.), salt(s), alcohol(s) such as, e.g., ethanol, diethanolamine, Britton-Robinson buffer, lactate, acetate, glutamate, glycine, citrate, succinate, surfactants, polysorbate(s), solubilizing polymers, such as polyethylene glycol(s), inorganic or organic acids such as methanesulfonic acid, lactic acid, tartaric acid, citric acid, succinic acid, hydrochloric acid, hydrobromic acid, sulfuric acid, nitric acid, ethanesulfonic acid, p-toluenesulfonic acid, salicylic acid and the like, choline, n-methyl glucamine, diethylamine, procaine and the like.

In some aspects, the reconstituted formulation of the present disclosure has an osmolarity of between about 250 milliOsmoles/liter (mOsm) and about 350 mOsm; or between about 280 mOsm and about 320 mOsm; or between about 290 mOsm and about 310 mOsm.

The present disclosure provides methods and formulations enabling the provision of glyburide formulations having significantly higher glyburide solubility in the dosing solutions, i.e., about 3-fold higher than prior art intravenous glyburide dosing solutions (i.e., greater than 15 µg/ml in contrast to less than 5.7 µg/ml in prior art intravenous glyburide dosing solutions). Further, there is no detectable loss of glyburide due to precipitation or sorption even at these three-fold higher concentrations.

In some aspects, a diluted (also referred to herein as the "final dosing" formulation) glyburide formulation according to the present disclosure has a glyburide concentration of 7.2 (±0.2) µg/mL and infusion pH to ~8.3 (±0.1).

In some aspects, a final dosing glyburide formulation has a pH of 7.8 to 9.0, 7.9 to 9.0, 8.0 to 9.0. In some aspects, a final dosing glyburide formulation has a pH of 7.8 to 9, 7.9, 8.0, 8.1, 8.2, 8.3, 8.4, 8.5, 8.6, 8.7, 8.8, or 8.9.

In some aspects, a final dosing glyburide formulation has a buffer concentration of about 0.1 to 0.5 mM, about 0.15 to 0.4 mM, about 0.2 to 0.3 mM, or about 0.2 mM.

In some aspects, a diluted glyburide formulation of the present disclosure is diluted into 500 mL IV infusion bag, thereby reducing the amount of infusion liquids administered to the subject. In view of the increased solubility, stability, and minimized sorption to medical containers, the formulation of the present disclosure makes it possible to use a more concentrated dosing formulation, thereby delivering a consistent therapeutic dose over the infusion period while using significantly less infusion fluids.

In some aspects, the present disclosure provides a method for decreasing the volume of infusion liquids administered to the subject by about 25-30% over the infusion period, e.g., from about 2 L to 1.5 L for a four day infusion period or from about 1.5 L to 1.1 L for a three day infusion period.

In some aspects, due to the advantages of the present invention, a diluted glyburide formulation can be administered at a slower rate than prior art intravenous glyburide formulations. For example, the infusion rates can be decreased to about 80% the rate of infusion used for infusing prior art intravenous glyburide formulations, e.g., 23 ml/hour for first six hours and 15.9 ml/hour thereafter versus 29 ml/hour for first six hours and 20 ml/hour thereafter compared to prior art intravenous glyburide formulations.

In some aspects, the present disclosure includes sterilizing the formulations of the present disclosure. In some aspects, the formulation may be filter sterilized. In some aspects, the formulation may be sterilized to have zero bioburden. In some aspects, the product of the present disclosure may be terminally sterilized. In some aspects, the product is sterilized with gamma irradiation. In some aspects, the product is sterilized by electron beam, X-ray, hydrogen peroxide, or ethylene oxide. In some aspects, the product may be a powder, a solution, a vial, a kit, a prefilled syringe, an injection device, a cartridge, an on body injector, an auto-injector, an infusion bag, or any other container or container set suitable for storage, infusion and/or injection of the products of the present disclosure. In some aspects, the product satisfies a "sterility assurance level" or "SAL" of 10-3, 10-4, or 10-6.

Kits having features of the invention may include liquid solutions of glyburide, and/or liquid solutions of glyburide together with one or more compounds, and may include instructions for the use of such liquid solutions. For example, instructions for the use of such liquid solutions may include instructions for freeze-drying such solutions in order to obtain a lyophilized formulation of the compound or compounds of interest. Alternatively, or in addition, kits having features of the invention may include lyophilized formulations of glyburide, and/or lyophilized formulations of glyburide together with one or more compounds, and/or lyophilized formulations of glyburide together with one or more liquids for reconstitution, and may include instructions for the use of such lyophilized formulations. For example, instructions for the use of such lyophilized formulations may include instructions for re-constituting such lyophilized formulations to provide solutions, preferably sterile solutions, suitable for use in pharmaceutical application. In some aspects, the vial contains the buffer of the present disclosure at a concentration of 6 to 40 mM, 7 to 30 mM, 8 to 25 mM, 9 to 20 mM, or 10 to 15 mM.

In some aspects, the present disclosure includes methods of using the following exemplary items:

1. A formulation comprising:
   a) glyburide or a pharmaceutically acceptable salt thereof;
   b) a buffering agent;
   c) a base; and
   d) a sugar alcohol,
   wherein the formulation has a pH outside of the buffering capacity of the buffering agent, and
   wherein the buffering agent has a pKa of 7.7 to 9.2.
2. The formulation of any preceding item, wherein the pharmaceutically acceptable salt thereof is a sodium addition salt.
3. The formulation of any preceding item, wherein the glyburide or pharmaceutically acceptable salt thereof is about 2.7 to 3.1% (w/w) of the formulation.
4. The formulation of any preceding item, wherein the sugar alcohol is about 84 to 90% w/w of the formulation.
5. The formulation of any preceding item, comprising the sugar alcohol and the glyburide or pharmaceutically acceptable salt thereof in a weight ratio of 28 to 35:1.
6. The formulation of any preceding item, wherein, upon storage for 12 months at 25° C./60% relative humidity (RH), has a pH that is within about 0.2 pH unit of the formulation prior to storage, or wherein, upon storage for 6 months at 40° C./75% RH, has a pH that is within about 0.2 pH unit of the formulation prior to storage, or wherein, upon storage for 4 weeks at 70° C./75% RH, has a pH that is within about 0.2 pH unit of the formulation prior to storage.
7. The formulation of any preceding item, wherein the buffering agent is a buffer having a pH of 7.8 to 9.
8. The formulation of any preceding item, comprising the base and the glyburide or pharmaceutically acceptable salt thereof in a ratio so the formulation has a pH of 10.1 to 10.9 when reconstituted in water for injection (WFI).
9. The formulation of any preceding item, wherein the formulation comprises the sugar alcohol and the glyburide or pharmaceutically acceptable salt thereof in a weight ratio of 27 to 40:1.
10. The formulation of any preceding item, wherein the formulation comprises the sugar alcohol and the buffering agent in a weight ratio of 8 to 12:1.
11. The formulation of any preceding item, wherein the formulation comprises 26 to 34 mg/ml of the sugar alcohol.
12. The formulation of any preceding item, wherein the base and the glyburide or pharmaceutically acceptable salt thereof have a molar ratio of 5.4 to 6.3:1.
13. The formulation of any preceding item, wherein the formulation comprises about 8 to 12% (w/w) of the buffering agent.
14. The formulation of any preceding item, wherein the formulation is free of cyclodextrins.
15. A formulation comprising:
   e) glyburide or a pharmaceutically acceptable salt thereof;
   f) a buffering agent;
   g) a base; and
   h) a sugar alcohol,
   wherein the formulation has a pH outside of the buffering capacity of the buffering agent, and
   wherein the formulation is free of cyclodextrins.
16. The formulation of item 15, wherein the glyburide or pharmaceutically acceptable salt thereof is about 2.7 to 3.1% (w/w) of the formulation, and/or wherein the sugar alcohol is about 84 to 90% (w/w) of the formulation.
17. The formulation of item 15, comprising the sugar alcohol and the glyburide or pharmaceutically acceptable salt thereof in a weight ratio of 28 to 35:1.

18. The formulation of item 15, wherein, upon storage for 12 months at 25° C./60% relative humidity (RH), has a pH that is within about 0.2 pH unit of the formulation prior to storage, or wherein, upon storage for 6 months at 40° C./75% RH, has a pH that is within about 0.2 pH unit of the formulation prior to storage, or wherein, upon storage for 4 weeks at 70° C./75% RH, has a pH that is within about 0.2 pH unit of the formulation prior to storage.
19. The formulation of item 15, wherein the buffering agent is a buffer having a pH of 7.8 to 9.
20. The formulation of item 15, comprising the base and the glyburide or pharmaceutically acceptable salt thereof in a ratio so the formulation has a pH of 10.1 to 10.9 when reconstituted in water for injection (WFI).
21. The formulation of item 15, wherein the formulation comprises the sugar alcohol and the glyburide or pharmaceutically acceptable salt thereof in a weight ratio of 27 to 40:1.
22. The formulation of item 15, wherein the formulation comprises the sugar alcohol and the buffering agent in a weight ratio of 8 to 12:1.
23. The formulation of item 15, wherein the formulation comprises 26 to 34 mg/ml of the sugar alcohol.
24. The formulation of item 15, wherein the base and the glyburide or pharmaceutically acceptable salt thereof have a molar ratio of 5.4 to 6.3:1.
25. The formulation of item 15, wherein the formulation comprises about 8 to 12% (w/w) of the buffering agent, and wherein the buffering agent has a pKa of 7.7 to 9.2.

Following is an exemplary dosing schedule. References to mass refer to the SUR1-TRPM4 channel inhibitor in the drug only (placebo has none).

TABLE 1

Dosing Regimen

| | 0 to 24 Hours | | >24 to 48 Hours | >48 to 72 Hours |
|---|---|---|---|---|
| | Bolus | Infusion | Infusion | Infusion |
| Concentration | 5.3 µg/mL | 5.3 µg/mL | 5.3 µg/mL | 5.3 µg/mL |
| Dose | 0.13 mg | 2.99 mg | 2.67 mg | 2.67 mg |
| Total Volume | 24 mL | 564 mL | 504 mL | 504 mL |
| Dose/hr | 3.9 mg/hr | 0.16 mg/hr | 0.11 mg/hr | 0.11 mg/hr | 0.11 mg/hr |
| Volume/hr | 720 mL/hr | 31 mL/hr | 21 mL/hr | 21 mL/hr | 21 mL/hr |
| Duration | 2 min (±1 min) | 6 hrs (±5 min) | 18 hrs (±5 min) | 24 hrs (±10 min) | 24 hrs (±10 min) |

Unlike clot busters that are typically administered to subjects with ischemic stroke, SUR1-TRPM4 channel inhibitors do not result in bleeding. Therefore, SUR1-TRPM4 channel inhibitors can be effective both when they are first administered quickly after the injury or condition, or some time period after the injury or condition that relates to cerebral edema occurs. In one embodiment, the first administration of the SUR1-TRPM4 channel inhibitor can be within the first hour, first 2 hours, first 3 hours, first four 4 hours, first 6 hours, first 8 hours, or first 10 hours of the injury or condition occurring. In another embodiment, the first administration of the SUR1-TRPM4 channel inhibitor can be at a time period after the injury or condition related to cerebral edema occurs of at least 4 hours, at least than 4½ hours (the time period at which clot busters can be ineffective or even dangerous), at least 6 hours, at least 8 hours, or at least 10 hours. In other examples, the first administration of the SUR1-TRPM4 channel inhibitor can be at a time period within 6 hours after the injury or condition occurs. In further embodiments, the first administration of the SUR1-TRPM4 channel inhibitor can be at a time period after 6 hours of the injury or condition occurring. In another embodiment, the first administration can be within 8 hours of the injury or condition occurring. In additional embodiments, the first administration of the SUR1-TRPM4 channel inhibitor can be at a time period within 10 hours of the injury or condition occurring.

The inventive methods are compatible with existing treatments for ischemic stroke. It is, thus, contemplated that the methods may be employed with thrombolytic therapies, such as tissue plasminogen activator (tPA) and similar thrombolytic agents. They may also be employed in patients undergoing decompressive craniectomy to address space occupying edema.

Assessing Outcomes

Further, the present disclosure is drawn to a method of improving outcomes, which are generally assessed by measuring the degree of disability in a subject that has suffered from a stroke.

For example, an improved difference in degree of disability can be realized that is at least about 10% based on the stroke scoring system(s). In other embodiments, the reduction of the degree of disability can be at least about 15%, at least about 20%, at least about 25%, or at least about 30%. The scoring system can be based upon a National Institutes of Health stroke score system (NIHSS), the modified Rankin Scale, a Barthel Index, or the size of the lesion as measured on CT and/or MRI. In one example, the first scoring system or test might be based on the NIHSS, and the second scoring system or test can be based on the modified Rankin Scale or the Barthel Index or the NIHSS.

The Modified Rankin Scale

The mRS, the most commonly use assessment in stroke, rates global disability following stroke and assessment at 90 days is the most widely used primary outcome measure used in acute stroke trials. It is an ordinal, hierarchical scale that rates disability on a scale from 0 (no symptoms) to 6 (death).
  0—No symptoms.
  1—No significant disability. Able to carry out all usual activities, despite some symptoms.
  2—Slight disability. Able to look after own affairs without assistance, but unable to carry out all previous activities.
  3—Moderate disability. Requires some help, but able to walk unassisted.
  4—Moderately severe disability. Unable to attend to own bodily needs without assistance, and unable to walk unassisted.
  5—Severe disability. Requires constant nursing care and attention, bedridden, incontinent.
  6—Dead.

Although the mRS has often been analyzed as a dichotomous outcome (e.g., defining "good" and "bad" outcomes as above and below a threshold, such as 0-3 versus 4-6), this approach often diminishes the power to detect an effect and, in fact, has been found to obscure both positive and negative effects. In contrast, ordinal analysis retains the full power of the mRS and better reflects health status by valuing each transition. In the case of severe strokes, the mRS is sometimes analyzed by collapsing the scale at each end (e.g., combining 0-1 and 5-6) on the basis that there is no meaningful difference between those outcomes—the difference between fully normal and functionally normal is not meaningful and the difference between dead and being bedridden and unable to carry out even basic functions is also not meaningful. Thus, the abbreviated scale 0-1, 2, 3, 4, 5-6 may still be analyzed as an ordinal scale, using, for example, the Mann-Whitney test or other suitable statistic that essentially asks if two distributions are different from one another. A common odds ratio can be estimated, using, for example, ordinal logistic regression, in order to assess the magnitude of any effect detected, and whether the effect favors drug or placebo. An odds ratio exceeding 1, indicates a favorable drug response. Thus, the invention contemplates that the drug will have an odds ratio greater than 1 in the treated population versus a placebo control. In some cases the odds ratio may exceed 1.2, which not only is strong evidence of effectiveness, it represents a clearly, clinically meaningful benefit.

The Barthel Index

The Barthel Index ("BI") assesses functionality based on activities of daily living. The BI employs 10 domains that describe activities of daily living and mobility. Higher scores are better and indicate a higher level of functional independence. The BI assesses the following ten different domains and 100-point scoring system:

Presence or absence of fecal incontinence
 0=incontinent (or needs to be given enemas)
 5=occasional accident
 10=continent
Presence or absence of urinary incontinence
 0=incontinent, or catheterized and unable to manage alone
 5=occasional accident
 10=continent
Help needed with grooming
 0=needs to help with personal care
 5=independent face/hair/teeth/shaving (implements provided)
Help needed with toilet use
 0=dependent
 5=needs some help, but can do something alone
 10-independent (on and off, dressing, wiping)
Help needed with feeding
 0=unable
 5=needs help cutting, spreading butter, etc., or requires modified diet
 10=independent
Help needed with transfers (e.g. from chair to bed)
 0=unable, no sitting balance
 5=major help (one or two people, physical), can sit
 10=minor help (verbal or physical)
 15=independent
Help needed with walking
 0=immobile or <50 yards
 5=wheelchair independent, including corners, >50 yards
 10=walks with help of one person (verbal or physical) >50 yards
 15=independent (but may use any aid; for example, stick)>50 yards
Help needed with dressing
 0=dependent
 5=needs help but can do about half unaided
 10=independent (including buttons, zips, laces, etc.)
Help needed with climbing stairs
 0=unable
 5=needs help (verbal, physical, carrying aid)
 10=independent
Help needed with bathing
 0=dependent
 5=independent (or in shower)

The NIH Stroke Scale Score

The NIH Stroke Scale Score (NIHSS) is used to quantify the level of impairment in a stroke patient. The NIHSS is composed of 11 items, with each scored between 0 and 4, with a score of 0 typically indicating normal function and a higher score indicating some level of impairment. The NIHSS is typically used to assess the severity of a stroke at baseline/presentation, but the numerical values may also be used to assess improvements in individual stroke patients or to compare the relative improvements between two groups of patients, such as placebo and drug-treated groups. The items assessed are as follows:

Item 1a: Level of Consciousness (LOC) Instructions

The investigator must choose a response if a full evaluation is prevented by such obstacles as an endotracheal tube, language barrier, orotracheal trauma/bandages. A 3 is scored only if the patient makes no movement (other than reflexive posturing) in response to noxious stimulation. Item 1a is scored as follows:
 0=Alert; keenly responsive.
 1=Not alert; but arousable by minor stimulation to obey, answer, or respond.
 2=Not alert; requires repeated stimulation to attend, or is obtunded and requires strong or painful stimulation to make movements (not stereotyped).
 3=Responds only with reflex motor or autonomic effects, or totally unresponsive, flaccid, and areflexic.

Item 1b: LOC Questions

The patient is asked the month and his/her age. The answer must be correct—there is no partial credit for being close. Aphasic and stuporous patients who do not comprehend the questions will score 2. Patients unable to speak because of endotracheal intubation, orotracheal trauma, severe dysarthria from any cause, language barrier, or any other problem not secondary to aphasia are given a 1. It is important that only the initial answer be graded and that the examiner not "help" the patient with verbal or non-verbal cues. Item 1b is scored as follows:
 0=Answers both questions correctly.
 1=Answers one question correctly.
 2=Answers neither question correctly.

Item 1c: LOC Commands

The patient is asked to open and close the eyes and then to grip and release the non-paretic hand. Substitute another one-step command if the hands cannot be used. Credit is given if an unequivocal attempt is made but not completed due to weakness. If the patient does not respond to command, the task should be demonstrated to him or her (pantomime), and the result scored (i.e., follows none, one, or two commands). Patients with trauma, amputation, or other physical impediments should be given suitable one-step commands. Item 1c is scored as follows:
 0=Performs both tasks correctly.
 1=Performs one task correctly.
 2=Performs neither task correctly.

Item 2: Best Gaze

Only horizontal eye movements will be tested. Voluntary or reflexive (oculocephalic) eye movements will be scored, but caloric testing is not done. If the patient has a conjugate deviation of the eyes that can be overcome by voluntary or reflexive activity, the score will be 1. If a patient has an isolated peripheral nerve paresis (CN III, IV, or VI), score a 1. Gaze is testable in all aphasic patients. Patients with ocular trauma, bandages, pre-existing blindness, or other disorder of visual acuity or fields should be tested with reflexive movements, and a choice made by the investigator. Establishing eye contact and then moving about the patient from side to side will occasionally clarify the presence of a partial gaze palsy. Item 2 is scored as follows:

0=Normal.

1=Partial gaze palsy; gaze is abnormal in one or both eyes, but forced deviation or total gaze paresis is not present.

2=Forced deviation, or total gaze paresis is not overcome by the oculocephalic maneuver.

Item 3: Visual Instructions

Visual fields (upper and lower quadrants) are tested by confrontation, using finger counting or visual threat, as appropriate. Patients may be encouraged, but if they look at the side of the moving fingers appropriately, this can be scored as normal. If there is unilateral blindness or enucleation, visual fields in the remaining eye are scored. Score 1 only if a clear-cut asymmetry, including quadrantanopia, is found. If patient is blind from any cause, score 3. Double simultaneous stimulation is performed at this point. If there is extinction, patient receives a 1, and the results are used to respond to item 11. Item 3 is scored as follows:

0=No visual loss.

1=Partial hemianopia.

2=Complete hemianopia.

3=Bilateral hemianopia (blind including cortical blindness).

Item 4: Facial Palsy Instructions

Ask—or use pantomime to encourage—the patient to show teeth or raise eyebrows and close eyes. Score symmetry of grimace in response to noxious stimuli in the poorly responsive or non-comprehending patient. If facial trauma/bandages, orotracheal tube, tape, or other physical barriers obscure the face, these should be removed to the extent possible. Item 4 is scored as follows:

0=Normal symmetrical movements.

1=Minor paralysis (flattened nasolabial fold, asymmetry on smiling).

2=Partial paralysis (total or near-total paralysis of lower face).

3=Complete paralysis of one or both sides (absence of facial movement in the upper and lower face).

Item 5: Motor Arm Instructions

The limb is placed in the appropriate position: extend the arms (palms down) 90 degrees (if sitting) or 45 degrees (if supine). Drift is scored if the arm falls before 10 seconds. The aphasic patient is encouraged using urgency in the voice and pantomime, but not noxious stimulation. Each limb is tested in turn, beginning with the non-paretic arm. Only in the case of amputation or joint fusion at the shoulder, the examiner should record the score as untestable (UN) and clearly write the explanation for this choice. Item 5 is scored as follows:

0=No drift; limb holds 90 (or 45) degrees for full 10 seconds.

1=Drift; limb holds 90 (or 45) degrees, but drifts down before full 10 seconds; does not hit bed or other support.

2=Some effort against gravity; limb cannot get to or maintain (if cued) 90 (or 45) degrees, drifts down to bed, but has some effort against gravity.

3=No effort against gravity; limb falls.

4=No movement.

UN=Amputation or joint fusion, explain:

Item 6: Motor Leg Instructions

The limb is placed in the appropriate position: hold the leg at 30 degrees (always tested supine). Drift is scored if the leg falls before 5 seconds. The aphasic patient is encouraged using urgency in the voice and pantomime, but not noxious stimulation. Each limb is tested in turn, beginning with the non-paretic leg. Only in the case of amputation or joint fusion at the hip, the examiner should record the score as untestable (UN) and clearly write the explanation for this choice. Item 6 is scored as follows:

0=No drift; leg holds 30-degree position for full 5 seconds.

1=Drift; leg falls by the end of the 5-second period but does not hit the bed.

2=Some effort against gravity; leg falls to bed by 5 seconds but has some effort against gravity.

3=No effort against gravity; leg falls to bed immediately.

4=No movement.

UN=Amputation or joint fusion, explain:

Item 7: Limb Ataxia Instructions

This item is aimed at finding evidence of a unilateral cerebellar lesion. Test with eyes open. In case of visual defect, ensure testing is done in intact visual field. The finger-nose-finger and heel-shin tests are performed on both sides, and ataxia is scored only if present out of proportion to weakness. Ataxia is absent in the patient who cannot understand or is paralyzed. Only in the case of amputation or joint fusion, the examiner should record the score as untestable (UN) and clearly write the explanation for this choice. In case of blindness, test by having the patient touch nose from extended arm position. Item 7 is scored as follows:

0=Absent.

1=Present in one limb.

2=Present in two limbs.

UN=Amputation or joint fusion, explain:

Item 8: Sensory Instructions

Sensation or grimace to pinprick when tested, or withdrawal from noxious stimulus in the obtunded or aphasic patient. Only sensory loss attributed to stroke is scored as abnormal and the examiner should test as many body areas [arms (not hands), legs, trunk, face] as needed to accurately check for hemisensory loss. A score of 2, "severe or total sensory loss," should only be given when a severe or total loss of sensation can be clearly demonstrated. Stuporous and aphasic patients will, therefore, probably score 1 or 0. The patient with brainstem stroke who has bilateral loss of sensation is scored 2. If the patient does not respond and is quadriplegic, score 2. Patients in a coma (item 1a=3) are automatically given a 2 on this item. Item 8 is scored as follows:

0=Normal; no sensory loss.

1=Mild-to-moderate sensory loss; patient feels pinprick is less sharp or is dull on the affected side; or there is a loss of superficial pain with pinprick, but patient is aware of being touched.

2=Severe or total sensory loss; patient is not aware of being touched in the face, arm, and leg.

Item 9: Best Language Instructions

A great deal of information about comprehension will be obtained during the preceding sections of the examination. For this scale item, the patient is asked to describe what is happening in the attached picture, to name the items on the attached naming sheet, and to read from the attached list of sentences. See the NIH Stroke Scale document pages 9 and 10 (ninds.nih.gov/health-information/public-education/know-stroke/health-professionals/nih-stroke-scale). Comprehension is judged from responses here, as well as to all of the commands in the preceding general neurological exam. If visual loss interferes with the tests, ask the patient to identify objects placed in the hand, repeat, and produce speech. The intubated patient should be asked to write. The patient in a coma (item 1a=3) will automatically score 3 on this item. The examiner must choose a score for the patient with stupor or limited cooperation, but a score of 3 should be used only if the patient is mute and follows no one-step commands. Item 9 is scored as follows:

0=No aphasia; normal.

1=Mild-to-moderate aphasia; some obvious loss of fluency or facility of comprehension, without significant limitation on ideas expressed or form of expression. Reduction of speech and/or comprehension, however, makes conversation about provided materials difficult or impossible. For example, in conversation about provided materials, examiner can identify picture or naming card content from patient's response.

2=Severe aphasia; all communication is through fragmentary expression; great need for inference, questioning, and guessing by the listener. Range of information that can be exchanged is limited; listener carries burden of communication. Examiner cannot identify materials provided from patient response.

3=Mute, global aphasia; no usable speech or auditory comprehension.

Item 10: Dysarthria Instructions

If patient is thought to be normal, an adequate sample of speech must be obtained by asking patient to read or repeat words from the NIH Stroke Scale document pages 11 and 12. If the patient has severe aphasia, the clarity of articulation of spontaneous speech can be rated. Only if the patient is intubated or has other physical barriers to producing speech, the examiner should record the score as untestable (UN) and clearly write the explanation for this choice. Do not tell the patient why he/she is being tested. Item 10 is scored as follows:

0=Normal.

1=Mild-to-moderate dysarthria; patient slurs at least some words and, at worst, can be understood with some difficulty.

2=Severe dysarthria; patient's speech is so slurred as to be unintelligible in the absence of or out of proportion to any dysphasia, or is mute/anarthric.

UN=Intubated or other physical barrier, explain:

Item 11: Extinction and Inattention Instructions (Formerly Neglect)

Sufficient information to identify neglect may be obtained during the prior testing. If the patient has a severe visual loss preventing visual double simultaneous stimulation, and the cutaneous stimuli are normal, the score is normal. If the patient has aphasia but does appear to attend to both sides, the score is normal. The presence of visual spatial neglect or anosagnosia may also be taken as evidence of abnormality. Since the abnormality is scored only if present, the item is never untestable. Item 11 is scored as follows:

0=No abnormality.

1=Visual, tactile, auditory, spatial, or personal inattention, or extinction to bilateral simultaneous stimulation in one of the sensory modalities.

2=Profound hemi-inattention or extinction to more than one modality; does not recognize own hand or orients to only one side of space.

The individual scores from the 11 items are summed to obtain a patient's total NIHSS score. The maximum possible score is 42 and the minimum score is 0. The NIHSS can be keyed to stroke severity as follows:

| NIHSS | Severity |
|---|---|
| 0 | No stroke symptoms |
| 1-4 | Minor stroke |
| 5-15 | Moderate stroke |
| 16-20 | Moderate to severe stroke |
| 21-42 | Severe stroke |

Patients treated according to the invention may have an NIHSS of at least 10, e.g., 10-20. Life threatening swelling can occur in up to 8% of hospitalized ischemic stroke patients and up to 15% of all middle cerebral artery (MCA) strokes. Patients that progress to such swelling may present with a National Institute of Heath Stroke Score (NIHSS) typically greater than 20 when the dominant hemisphere is involved, and greater than 15 when the nondominant hemisphere is involved. In other examples, most (perhaps more than 99%) of cases that go on to develop significant swelling have an NIHSS≥10. Patients under an NIHSS score of 10 do not tend to develop life threatening swelling.

Definitions and Interpretation

In describing and claiming the present invention, the following terminology will be used.

The singular forms "a," "an," and "the" include plural referents unless the context clearly dictates otherwise. Thus, for example, reference to "a SUR1-TRPM4 channel inhibitor" includes reference to one or more of such SUR1-TRPM4 channel inhibitors.

As used herein, the term "active agent" indicates a compound or mixture of compounds that when added to a composition, tend to produce a particular therapeutic effect.

As used herein, the term "Large Hemispheric Infarction" or "LHI" refers to an ischemic stroke affecting the total or sub-total territory of the middle cerebral artery (MCA), with or without involvement of the adjacent (i.e., anterior cerebral artery [ACA] or posterior cerebral artery [PCA]) territories).

The term "lesion" refers to an abnormality in the tissue of the brain. In some instances, a lesion can be a space-occupying lesion that has recognizable volume and can impinge on nearby tissues and blood vessels.

As used herein, the term "placebo" is a formulation that does not contain a SUR1-TRPM4 antagonist, or is compositionally similar with the exception that the amounts (wt %) of a SUR1-TRPM4 channel inhibitor is replaced with the same amount (wt %) of other inert ingredients, e.g., water. Additionally, the "placebo" may have slight formulation differences that are typical due to the absence of the drug, as understood by those in the art.

The term "subject" as used herein includes all members of the animal kingdom, including mammals, and most typically, refers to human patients.

The term "sulfonylureas" includes sulfonylureas, sulfonylurea mimetics, and any other composition that is effective to block or reduce activity associated with the channels of SUR1.

"Stroke" occurs when there is poor blood flow to the brain, and can result in cellular death. As defined herein, there are essentially two known types of strokes, namely ischemic stroke or hemorrhagic stroke. Ischemic stroke occurs when there is a lack of blood flow to the brain, and hemorrhagic stroke occurs when there is bleeding in the cranial vault or when there is bleeding within the brain tissue and includes subarachnoid hemorrhage and intracerebral hemorrhage. Both forms can lead to cerebral edema.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one embodiment, the degree of flexibility can be within about ±10% of the numerical value. In another embodiment, the degree of flexibility can be within about ±5% of the numerical value. In a further embodiment, the degree of flexibility can be within about ±2%, ±1%, or ±0.05%, of the numerical value.

Generally, herein, the term "or" includes "and/or."

As used herein, a plurality of active agents, compounds, injuries or conditions, etc., may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

As used herein, all percent compositions are given as weight-percentages, unless otherwise stated. When solutions of components are referred to, percentages refer to weight-percentages of the composition including solvent (e.g., water) unless otherwise indicated.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" would find direct support due to this definition.

As used herein, a plurality of compounds or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Furthermore, certain compositions, injuries or conditions, steps, or the like may be discussed in the context of one specific embodiment. It is understood that this is merely for convenience, and such disclosure is equally applicable to other embodiments found herein. For example, a list of active agents or drugs described with respect to a method of treating late neurological deterioration or death would find direct support for embodiments related to methods of reducing cerebral midline shift, even if those drugs are not re-listed in the context of that embodiment in the specification.

Embodiments of the present disclosure will be described with reference to the following Examples, which are provided for illustrative purposes only and should not be used to limit the scope of or construe the invention.

Example

The CHARM trial evaluated the safety and efficacy of intravenous glibenclamide as a treatment for large hemispheric infarction (LHI) patients at high risk for cerebral edema.

Patients meeting the following criteria were included:
A clinical diagnosis of acute ischemic stroke in the middle cerebral artery (MCA) territory.
A large hemispheric infarction defined as; lesion volume of 80 to 300 centimeters cubed ($cm^3$) on magnetic resonance imaging (MRI) diffusion-weighted imaging (DWI), or computed tomography perfusion (CTP), or an Alberta Stroke Program Early CT Score (ASPECTS) of 1 to 5 with involvement of at least 2 defined cortical regions.

Screening National Institutes of Health Stroke Scale (NIHSS)>=10.

At the time of randomization, and in the Investigator's judgement, it must be feasible for study drug treatment infusion to be initiated no later than 10 hours after time of symptom onset, if known, or the time last known normal.

Participants who wake with stroke may be included if neurological and other exclusion criteria are satisfied. The time of stroke onset is to be taken as the midpoint between sleep onset (or last known to be normal) and time of waking.

For participants who receive thrombectomy, inclusion into the study must be based on post-thrombectomy MRI-DWI.

Patients meeting the following criteria were excluded:

Participant is likely to have supportive care withdrawn on the first day.

Commitment to decompressive craniectomy (DC) prior to enrollment.

Evidence of concurrent infarction in the contralateral hemisphere sufficiently serious so as to affect functional outcome.

Pre-Specified Primary Endpoint

Modified Rankin Scale (mRS) score at 90 days analyzed as a shift analysis using a 5-category ordinal scale with 0/1 and 5/6 collapsed. The primary efficacy analysis was pre-specified to be conducted in participants 18-70 years of age (inclusive) who were randomized and receive study treatment (the modified intent-to-treat [mITT] population].

Five hundred thirty-five subjects were enrolled, with 268 treated with placebo and 267 treated with intravenous glyburide. The mITT population (the primary analysis population), those participants aged ≤70 years who received any study drug, consisted of 431 subjects.

An analysis was conducted in the mITT population to examine effects on lesion volume in subjects who were enrolled with CTP or DWI volume >80 $cm^3$ (ASPECTS enrollment was excluded as it does not assess lesion volume). An interaction term between treatment arm and stroke volume was included in an ordinal logistic regression model with 90-day mRS as the dependent variable. Independent variables included age, sex, baseline NIHSS, world region, tissue plasminogen activator, and thrombectomy.

Of the 431 subjects that comprised the mITT population, 280 (65%) had baseline stroke volume assessed on CTP or DWI. The baseline infarct volume was 154±146 mL, which did not differ by treatment arm. The common odds ratio (cOR) decreased with increasing lesion volume, crossing the "no effect" point (cOR=1.0) at about 140 $cm^3$, indicating no drug effect above that threshold. Below 140 $cm^3$ the cOR increased with decreasing lesion volume, with a cOR of about 6 for the group of patients with a lesion volume between less than 85 $cm^3$, suggesting an extremely robust effect on the patients with smaller lesion volumes. There was a statistically significant interaction between glibenclamide and baseline stroke volume of ≤120 $cm^3$ (p=0.031), with a favorable outcome among glibenclamide-treated subjects in the ≤120 $cm^3$ subgroup (cOR 2.31, 95% CI 1.07-5.01, p=0.034).

The beneficial results were surprisingly drastically higher in the subjects that were administered glyburide in combination with thrombectomy (n=81). In those patients, there was a treatment-by-stroke volume interaction (p=0.009) and glibenclamide-treated subjects had a favorable outcome (cOR 4.69, 95% CI 1.10-20.1, p=0.037). In these subjects, the cOR crossed the "no effect" point (cOR=1.0) at about 180 $cm^3$ as shown in FIG. 1, indicating no drug effect above that threshold. Thus, the effects of combining glyburide administration with mechanical thrombectomy increased the pool of subjects that could benefit from the method and produced drastically higher functional benefits.

Thus, in the mITT patients who underwent thrombectomy, the cORs obtained were multiples higher than the overall population, indicating a particularly good response in the thrombectomy population.

What is claimed is:

1. A method of treating a patient diagnosed with an ischemic stroke with a lesion volume of 180 $cm^3$ or less, wherein the patient has experienced a wake-up stroke, comprising administering a SUR1-TRPM4 channel inhibitor to the patient.

2. The method of claim 1, wherein:
   a) the patient has undergone a mechanical thrombectomy before the administering step; or
   b) the administering begins prior to or during a mechanical thrombectomy.

3. The method of claim 1, wherein:
   a) the administering begins within 9 hours of the midpoint between sleep onset or last known to be normal and time of waking;
   b) the administering begins within 10 hours of the midpoint between sleep onset or last known to be normal and time of waking; or
   c) the administering begins within 8 hours of a first stroke symptom.

4. The method of claim 1, wherein the SUR1-TRPM4 channel inhibitor inhibits the SUR1 regulatory subunit.

5. The method of claim 1, wherein the SUR1-TRPM4 channel inhibitor comprises a member selected from the group consisting of glibenclamide, 4-trans-hydroxy-glibenclamide, 3-cis-hydroxyglibenclamide, tolbutamide, chlorpropamide, tolazamide, repaglinide, nateglinide, meglitinide, midaglizole, gliquidone, LY397364, LY389382, gliclazide, glimepiride, a sulfonylurea, a pharmaceutically acceptable salt thereof, a metabolite thereof that interacts with SUR1, and a combination thereof.

6. The method of claim 1, wherein the lesion volume is >50 $cm^3$ and <125 $cm^3$.

7. The method of claim 1, wherein the SUR1-TRPM4 channel inhibitor is glyburide or a pharmaceutically acceptable salt thereof in a formulation comprising a buffering agent, a base, and a sugar alcohol, wherein the formulation has a pH outside of the buffering capacity of the buffering agent, and wherein the buffering agent has a pKa of 7.7 to 9.2.

8. The method of claim 7, wherein the glyburide or pharmaceutically acceptable salt thereof is about 2.7 to 3.1% (w/w) of the formulation, and/or wherein the sugar alcohol is about 84 to 90% (w/w) of the formulation.

9. A method of treating a patient diagnosed with an ischemic stroke with a lesion volume of 180 $cm^3$ or less, comprising administering a SUR1-TRPM4 channel inhibitor to the patient in combination with a mechanical thrombectomy.

10. The method of claim 9, wherein the patient has undergone the mechanical thrombectomy before the administering step.

11. The method of claim 9, wherein the administering begins prior to or during the mechanical thrombectomy.

12. The method of claim 9, wherein the SUR1-TRPM4 channel inhibitor inhibits the SUR1 regulatory subunit.

13. The method of claim 9, wherein the SUR1-TRPM4 channel inhibitor comprises a member selected from the group consisting of glibenclamide, 4-trans-hydroxy-glibenclamide, 3-cis-hydroxyglibenclamide, tolbutamide, chlorpropamide, tolazamide, repaglinide, nateglinide, meglitinide, midaglizole, gliquidone, LY397364, LY389382, gliclazide, glimepiride, a sulfonylurea, a pharmaceutically acceptable salt thereof, a metabolite thereof that interacts with SUR1, and a combination thereof.

14. The method of claim 9, wherein the lesion volume is >50 cm$^3$ and <125 cm$^3$ or wherein the patient has experienced a wake-up stroke.

15. The method of claim 9, wherein the SUR1-TRPM4 channel inhibitor is glyburide or a pharmaceutically acceptable salt thereof in a formulation comprising a buffering agent, a base, and a sugar alcohol, wherein the formulation has a pH outside of the buffering capacity of the buffering agent, and wherein the buffering agent has a pKa of 7.7 to 9.2.

16. The method of claim 15, wherein the glyburide or pharmaceutically acceptable salt thereof is about 2.7 to 3.1% (w/w) of the formulation, and/or wherein the sugar alcohol is about 84 to 90% (w/w) of the formulation.

17. A method of treating a patient diagnosed with an ischemic stroke with a lesion volume of >50 cm$^3$ and <125 cm$^3$, comprising administering a SUR1-TRPM4 channel inhibitor to the patient in combination with a mechanical thrombectomy.

18. The method of claim 17, wherein the patient has undergone the mechanical thrombectomy before the administering step.

19. The method of claim 17, wherein the administering begins prior to or during the mechanical thrombectomy.

20. The method of claim 17, wherein the SUR1-TRPM4 channel inhibitor inhibits the SUR1 regulatory subunit.

21. The method of claim 17, wherein the SUR1-TRPM4 channel inhibitor comprises a member selected from the group consisting of glibenclamide, 4-trans-hydroxy-glibenclamide, 3-cis-hydroxyglibenclamide, tolbutamide, chlorpropamide, tolazamide, repaglinide, nateglinide, meglitinide, midaglizole, gliquidone, LY397364, LY389382, gliclazide, glimepiride, a sulfonylurea, a pharmaceutically acceptable salt thereof, a metabolite thereof that interacts with SUR1, and a combination thereof.

22. The method of claim 17, wherein the SUR1-TRPM4 channel inhibitor is glyburide or a pharmaceutically acceptable salt thereof in a formulation comprising a buffering agent, a base, and a sugar alcohol, wherein the formulation has a pH outside of the buffering capacity of the buffering agent, and wherein the buffering agent has a pKa of 7.7 to 9.2.

23. The method of claim 22, wherein the glyburide or pharmaceutically acceptable salt thereof is about 2.7 to 3.1% (w/w) of the formulation, and/or wherein the sugar alcohol is about 84 to 90% (w/w) of the formulation.

24. A method of treating a patient diagnosed with an ischemic stroke, wherein at the time of treatment the patient has (a) a lesion volume of at least 50 cm$^3$ on magnetic resonance imaging (MRI) diffusion-weighted imaging (DWI), or computed tomography perfusion (CTP), or (b) an Alberta Stroke Program Early CT Score (ASPECTS) of 1 to 5, and/or (c) a National Institutes of Health Stroke Scale (NIHSS) score ≥10 and ≤20; comprising administering a SUR1-TRPM4 channel inhibitor to the patient in combination with a mechanical thrombectomy.

25. The method of claim 24, wherein:
a) the patient has undergone the mechanical thrombectomy before the administering step; or
b) the administering begins prior to or during the mechanical thrombectomy.

26. The method of claim 24, wherein the SUR1-TRPM4 channel inhibitor inhibits the SUR1 regulatory subunit.

27. The method of claim 24, wherein the SUR1-TRPM4 channel inhibitor comprises a member selected from the group consisting of glibenclamide, 4-trans-hydroxy-glibenclamide, 3-cis-hydroxyglibenclamide, tolbutamide, chlorpropamide, tolazamide, repaglinide, nateglinide, meglitinide, midaglizole, gliquidone, LY397364, LY389382, gliclazide, glimepiride, a sulfonylurea, a pharmaceutically acceptable salt thereof, a metabolite thereof that interacts with SUR1, and a combination thereof.

28. The method of claim 24, wherein the patient has a lesion volume of >50 cm$^3$ and <125 cm$^3$ or wherein the patient has experienced a wake-up stroke.

29. The method of claim 24, wherein the SUR1-TRPM4 channel inhibitor is glyburide or a pharmaceutically acceptable salt thereof in a formulation comprising a buffering agent, a base, and a sugar alcohol, wherein the formulation has a pH outside of the buffering capacity of the buffering agent, and wherein the buffering agent has a pKa of 7.7 to 9.2.

30. The method of claim 29, wherein the glyburide or pharmaceutically acceptable salt thereof is about 2.7 to 3.1% (w/w) of the formulation, and/or wherein the sugar alcohol is about 84 to 90% (w/w) of the formulation.

* * * * *